US011633446B2

(12) United States Patent
Housey et al.

(10) Patent No.: US 11,633,446 B2
(45) Date of Patent: Apr. 25, 2023

(54) PLANT EXTRACTS WITH ANTI-DIABETIC AND OTHER USEFUL ACTIVITIES

(71) Applicant: Housey Pharmaceutical Research Laboratories, L.L.C., Southfield, MI (US)

(72) Inventors: Gerard M. Housey, Southfield, MI (US); Monica Elizabeth Balash, Farmington Hills, MI (US)

(73) Assignee: HOUSEY PHARMACEUTICAL RESEARCH LABORATORIES, L.L.C., Southfield, MI (US)

( * ) Notice: Subject to any disclaimer, the term of this patent is extended or adjusted under 35 U.S.C. 154(b) by 0 days.

(21) Appl. No.: 16/612,545

(22) PCT Filed: May 11, 2018

(86) PCT No.: PCT/US2018/032273
§ 371 (c)(1),
(2) Date: Nov. 11, 2019

(87) PCT Pub. No.: WO2018/209202
PCT Pub. Date: Nov. 15, 2018

(65) Prior Publication Data
US 2020/0197468 A1    Jun. 25, 2020

Related U.S. Application Data

(60) Provisional application No. 62/505,494, filed on May 12, 2017.

(51) Int. Cl.
| A61K 36/282 | (2006.01) |
| A23L 33/00 | (2016.01) |
| A61P 3/10 | (2006.01) |
| A61K 9/00 | (2006.01) |
| A61K 33/26 | (2006.01) |
| A61K 33/30 | (2006.01) |
| A61K 33/32 | (2006.01) |
| A61K 33/34 | (2006.01) |
| A61K 36/287 | (2006.01) |

(52) U.S. Cl.
CPC ............ *A61K 36/282* (2013.01); *A23L 33/30* (2016.08); *A61K 9/0053* (2013.01); *A61K 33/26* (2013.01); *A61K 33/30* (2013.01); *A61K 33/32* (2013.01); *A61K 33/34* (2013.01); *A61K 36/287* (2013.01); *A61P 3/10* (2018.01)

(58) Field of Classification Search
None
See application file for complete search history.

(56) References Cited

U.S. PATENT DOCUMENTS

| 5,260,200 A | 11/1993 | Kahn et al. |
| 5,858,701 A | 1/1999 | White et al. |
| 8,557,512 B2 | 10/2013 | Housey et al. |
| 2003/0072822 A1 | 4/2003 | Ribnicky et al. |
| 2008/0260924 A1 | 10/2008 | Chen et al. |
| 2010/0202980 A1 | 8/2010 | Fogel |
| 2011/0118180 A1 | 5/2011 | Silvestre et al. |
| 2011/0301182 A1 | 12/2011 | Dugi |
| 2012/0100223 A1 | 4/2012 | Bhagat |
| 2014/0302180 A1 | 10/2014 | Chapal et al. |
| 2016/0022752 A1 | 1/2016 | Housey et al. |
| 2018/0256660 A1 | 9/2018 | Housey et al. |

FOREIGN PATENT DOCUMENTS

| CN | 1 382 734 | 12/2002 |
| CN | 1 456 669 | 11/2003 |
| CN | 1994146 | 7/2007 |
| CN | 102178294 | 9/2011 |
| CN | 102 228 116 | 11/2011 |
| EP | 2 130 443 | 12/2009 |
| JP | 2005-505544 | 2/2005 |
| WO | 2003/020026 | 3/2003 |
| WO | 2008/121947 | 10/2008 |
| WO | 2010/010949 | 1/2010 |
| WO | 2014/165297 | 10/2014 |

OTHER PUBLICATIONS

Oxford Dictionary of Chemistry (7 ed.), 2016, Oxford University Press, Oxford, United Kingdom. Title page, publishing information, and table of contents, 3 pages.
"UNECE Standard FFV-22 concerning the marketing and commercial quality control of Lettuces, Curled-Leave Endives and Broad-Leaved (Batavian) Endives", Jan. 4, 2011, Agricultural Standards Unit Trade and Timber Division, United Nationals Economic Commission for Europe.
Acosta-Patiño, et al., "Hypoglycemic action of Cucurbita ficifolia on Type 2 diabetic patients with moderately high blood glucose levels", 2001, Journal of Ethnopharmacology, 77:99-101.
Ahmed, et al., "Acetylcholinesterase activity in the brain of alloxan diabetic albino rats: Presence of an inhibitor of this enzyme activity in the cerebral extract", Oct.-Dec. 2009, Int J Diab Dev Ctries, 29(4):174-177.
Ahmed, et al., "In vitro callus and in vivo leaf extract of Gymnema sylvestre stimulate β-cells regeneration and anti-diabetic activity in Wistar rats", 2010, Phytomedicine, 17:1033-1039.
Andrade-Cetto, et al., "Mexican plants with hypoglycaemic effect used in the treatment of diabetes", 2005, Journal of Ethnopharmacology, 99:325-348.
Backer, et al., "Phosphatidylinositol 3?-kinase is activated by association with IRS-1 during insulin stimulation", 1992, The EMBO Journal, 11(9):3469-3479.

(Continued)

*Primary Examiner* — Susan Hoffman
(74) *Attorney, Agent, or Firm* — Mueting Raasch Group

(57) ABSTRACT

This invention relates to plant extracts containing nutritionally beneficial or medicinally active compounds. Some of these extracts, or the purified compounds contained therein, may be used for the nutritional support, prevention, treatment, or possible cure of various metabolic and other diseases and disorders in human beings and animals, including type 1 and type 2 diabetes, by regulating insulin signaling. This regulatory effect may include modulations of the levels and/or activity of the Insulin Receptor (IR), the Insulin-like Growth Factor (IGF) Receptor, and/or the Insulin Receptor Substrate (IRS) proteins in cells and tissues in the body.

7 Claims, 6 Drawing Sheets

(56) References Cited

OTHER PUBLICATIONS

Barbieri, et al., "Glucose regulation and oxidative stress in healthy centenarians", 2003, Experimental Gerontology, 38:137-143.
Bazzano, et al., "Intake of Fruit, Vegetables, and Fruit Juices and Risk of Diabetes in Women", Jul. 2008, Diabetes Care, 31(7):1311-1317.
Berge, et al., "Pharmaceutical Salts", Jan. 1977, Journal of Pharmaceutical Sciences, 66(1):1-19.
Brownlee, "Banting Lecture 2004: The Pathobiology of Diabetic Complications: A Unifying Mechanism", Jun. 2005, Diabetes, 54:1615-1625.
Burks, et al., "IRS Pleckstrin Homology Domains Bind to Acidic Motifs in Proteins", Nov. 20, 1998, The Journal of Biological Chemistry, 273(47):31061-31067.
Buszewski, et al., "Hydrophilic interaction liquid chromatography (HILIC)—a powerful separation technique", 2012, Analytical and Bioanalytical Chemistry, 402:231-247. Published online Aug. 31, 2011.
Campbell, et al., "Metformin—life begins at 50", Sep./Oct. 2007, The British Journal of Diabetes and Vascular Disease, 7(5):247-252.
Carter, et al., "Fruit and vegetable intake and incidence of type 2 diabetes mellitus: systematic review and meta-analysis", 2010, BMJ-Online First, 341:c4229, 8 pages.
Clemmons, "Involvement of insulin-like growth factor-I in the control of glucose homeostasis", 2006, Current Opinion in Pharmacology, 6:620-625. Published online Oct. 9, 2006.
Database WPI, Week 200328, Thomson Scientific, London, GB, AN 2003-279525 & CN 1 382 734 A, (Lin Z), Dec. 4, 2002, 1 page.
Database WPI, Week 200416, Thomson Scientific, London, GB, AN 2004-157507 & CN 1 456 669 A, (Lin Z), Nov. 19, 2003, 1 page.
Database WPI, Week 201212, Thomson Scientific, London, GB, AN 2011-P91172 & CN 102 228 116 A, (Xuzhou Lvzhiye Biological Foodstuff Co), Nov. 2, 2011, 2 pages.
DeFronzo, "Pathogenesis of type 2 diabetes mellitus", 2004, Med Clin N Am, 88:787-835.
Deutschländer, et al., "Hypoglycemic evaluation of a new triterpene and other compounds isolated from *Euclea undulata Thunb.* var. *myrtina* (Ebenaceae) root bark", 2011, Journal of Ethnopharmacology, 133:1091-1095. Published online Nov. 24, 2010.
Diabetes Prevention Program Research Group, Massachusetts Medical Society, "Reduction in the incidence of type 2 diabetes with lifestyle intervention or metformin", Feb. 7, 2002, N Engl J Med, 346(6):393-403.
Diaz-Flores, et al., "Effect of an aqueous extract of Cucurbita ficifolia Bouché on the glutathione redox cycle in mice with STZ-induced diabetes", 2012, Journal of Ethnopharmacology, 144:101-108. Published online Sep. 1, 2012.
Dong, et al., "Inactivation of Hepatic Foxo1 by Insulin Signaling is Required for Adaptive Nutrient Homeostasis and Endocrine Growth Regulation", Jul. 2008, Cell Metabolism, 8:65-76.
DuPont, et al., "Effect of Variety, Processing, and Storage on the Flavonoid Glycoside Content and Composition of Lettuce and Endive", 2000, J Agri Food Chem, 48(9):3957-3964.
Estruch, et al., "Primary Prevention of Cardiovascular Disease with a Mediterranean Diet", 2013, N Eng J Med, 10.1056/NEJMoa1200303, 12 pages. Published online Feb. 25, 2013.
European Patent Application No. 14779967.0), filed Oct. 12, 2015; Extended European Search Report dated Sep. 9, 2016, 8 pages.
Fahey, et al., "The chemical diversity and distribution of glucosinolates and isothiocyanates among plants", 2001, Phytochemistry, 56:5-51.
Ghamarian, et al., "Effect of chicory seed extract on glucose tolerance test (GTT) and metabolic profile in early and late stage diabetic rats", 2012, DARU Journal of Pharmaceutical Sciences, 20:56, 9 pages.
Hagel, et al., "Got milk? The secret life of laticifers", 2008, Trends in Plant Science, 13(12):631-639. Published online Oct. 30, 2008.
Haj, et al., "Imaging Sites of Receptor Dephosphorylation by PTP1B on the Surface of the Endoplasmic Reticulum", Mar. 1, 2002, Science, 295:1708-1711.

Hamza, et al., "Treatment of high fat diet induced type 2 diabetes in C57BL/6J mice by two medicinal plants used in traditional treatment of diabetes in the east of Algeria", 2011, Journal of Ethnopharmacology, 133:931-933. Published online Nov. 19, 2010.
Hubbard, "Crystal structure of the activated insulin receptor tyrosine kinase in complex with peptide substrate and ATP analog", 1997, The EMBO Journal, 16(18):5572-5581.
Ide, et al., "SREBPs suppress IRS-2 mediated insulin signalling in the liver", Apr. 2004, Nature Cell Biology, 6 (4):351-357. Published online Mar. 14, 2004.
International Patent Application No. PCT/US2014/025114, filed Mar. 12, 2014; International Preliminary Report on Patentability dated Sep. 15, 2015; 7 pages.
International Patent Application No. PCT/US2014/025114, filed Mar. 12, 2014; International Search Report / Written Opinion dated Jul. 8, 2014; 9 pages.
International Patent Application No. PCT/US2018/032273, filed May 11, 2018, International Search Report / Written Opinion dated Aug. 8, 2018, 8 pages.
International Patent Application No. PCT/US2018/032273, filed May 11, 2018, International Preliminary Report on Patentability dated Nov. 12, 2019, 6 pages.
Jhala, et al., "cAMP promotes pancreatic β-cell survival via CREB-mediated induction of IRS2", 2003, Genes & Development, 17:1575-1580.
Jonsson, et al., "Insulin-promoter-factor 1 is required for pancreas development in mice", Oct. 13, 1994, Nature, 371:606-609.
Kamel, et al., "Effect of Cichorium endivia Leaves on Some Biochemical Parameters in Streptozotocin-Induced Diabetic Rats", 2011, Australian Journal of Basic and Applied Sciences, 5(7):387-396.
Kelly-Welch, et al., "Trangenic Expression of Insulin Receptor Substrate 2 in Murine B Cells Alters the Cell Density-Dependence of IgE Production in Vitro and Enhances Ig# Production in Vivo", 2004, J. Immunol. 172(5):2803-2810.
Koudela, et al., "Nutritional composition and yield of endive cultivars—*Cichorium endivia* L", 2007, Hort. Sci. 35 (1):6-10.
Krebs, et al., "A New Role for SOCS in Insulin Action", Feb. 11, 2003, Sci STKE, 2003:pe6, 3 pages.
Layne, "Characterization and comparison of the chromatographic performance of conventional, polar-embedded, and polar-endcapped reversed-phase liquid chromatography stationary phases", 2002, Journal of Chromatography A, 957:149-164.
Lewinsohn, et al., "The geographical distribution of plant latex", 1991, Chemoecology, 2:64-68.
Liu, et al., "A Prospective Study of Fruit and Vegetable Intake and the Risk of Type 2 Diabetes in Women", Dec. 2004, Diabetes Care, 27(12):2993-2996.
Manning, et al., "AKT/PKB Signaling: Navigating Downstream", Jun. 29, 2007, Cell, 129:1261-1274.
Mascherpa, et al., "Identification of Phenolic Constituents in *Cichorium endivia* Var. *crispum* and Var. *latifolium* Salads by High-Performance Liquid Chromatography with Diode Array Detection and Electrospray Ionization Tandem Mass Spectrometry", Nov. 19, 2012, Journal of Agricultural and Food Chemistry, 60:12142-12150.
Meier, et al., "Sustained beta cell apoptosis in patients with long-standing type 1 diabetes: indirect evidence for islet regeneration?", 2005, Diabetologia, 48:2221-2228. Published online Oct. 5, 2005.
Meyer, et al., "Carbohydrates, dietary fiber, and incident type 2 diabetes in older women", 2000, Am J Clin Nutr, 71:921-930.
Montagut, et al., "Oligomers of grape-seed procyanidin extract activate the insulin receptor and key targets of the insulin signaling pathway differently from insulin", 2010, J Nutr Biochem, 21:476-481.
Montonen, et al., "Food consumption and the incidence of type II diabetes mellitus", 2005, Eur J Clin Nutr, 59:441-448. Published online Jan. 12, 2005.
Muthusamy, et al., "Inhibition of protein tyrosine phosphatase 1B and regulation of insulin signalling markers by caffeoyl derivatives of chicory (*Cichorium intybus*) salad leaves", 2010, Br J Nutr, 104:813-823. Published online May 6, 2010.

(56) References Cited

OTHER PUBLICATIONS

Muthusamy, et al., "Tannins present in Cichorium intybus enhance glucose uptake and inhibit adipogenesis in 3T3-L1 adipocytes through PTP1B inhibition", 2008, Chem Biol Interact, 174:69-78. Published online Apr. 24, 2008.
Nakayama, et al., "Prime role for an insulin epitope in the development of type 1 diabetes in NOD mice", May 12, 2005, Nature, 435:220-223.
Obanda, et al., "Bioactives of *Artemisia dracunculus* L. Mitigate the Role of Ceramides in Attenuating Insulin Signaling in Rat Skeletal Muscle Cells", Mar. 2012, Diabetes, 61:597-605.
Papetti, et al. "Hydroxycinnamic acid derivatives occuring in Cichorium endivia vegetables", Sep. 29, 2008, Journal of Pharmaceutical and Biomedical Analysis, 48:472-476.
Papetti, et al., Anti- and Pro-oxidant Water Soluble Activity of *Cichorium* Genus Vegetables and Effect of Thermal Treatment, Jul. 31, 2002, J Agric Food Chem, 50:4696-4704.
Park, et al., "Drying Operational Parameters Influence on Chicory Roots Drying and Inulin Extraction", Sep. 2007, Food and Bioproducts Processing. 85(C3);184-192.
Petlevski, et al., "Effect of 'antidiabetis' herbal preparation on serum glucose and fructosamine in NOD mice", May 2001, J Ethnopharmacol, 75:181-184.
Petlevski, et al., "Glutathione S-Transferases and Malondialdehyde in the Liver of NOD Mice on Short-Term Treatment with Plant Mixture Extract P-9801091", Apr. 2003, Phytother Res, 17:311-314.
Pinent, et al., "Grape Seed-Derived Procyanidins Have an Antihyperglycemic Effect in Streptozotocin-Induced Diabetic Rats and Insulinomimetic Activity in Insulin-Sensitive Cell Lines", Nov. 2004, Endocrinology, 145(11):4985-4990.
Pushparaj, et al., "Anti-diabetic effects of Cichorium intybus in streptozotocin-induced diabetic rats", May 2007, J Ethnopharmacol, 111:430-434. Published online Dec. 1, 2006.
Pushparaj, et al., "Effects of Averrhoa bilimbi leaf extract on blood glucose and lipids in streptozotocin-diabetic rats", 2000, J Ethnopharmacol, 72:69-76.
Pushparaj, et al., "The mechanism of hypoglycemic action of the semi-purified fractions of Averrhoa bilimbi in streptozotocin-diabetic rats", 2001, Life Sciences, 70:535-547.
Roman-Ramos, et al., "Anti-hyperglycemic effect of some edible plants", 1995, J Ethnopharmacol, 48:25-32.
Semple, et al., "Postreceptor insulin resistance contributes to human dyslipidemia and hepatic steatosis", Feb. 2009, J Clin Invest, 119(2):315-322.
Shimano, "SREBP-1c and TFE3, energy transcription factors that regulate hepatic insulin signaling", May 2007, J Mol Med, 85:437-444. Published online Feb. 6, 2007.
Sun, et al., "Role of IRS-2 in insulin and cytokine signalling", Sep. 14, 1995, Nature, 377:173-177.
Sun, et al., "Structure of the insulin receptor substrate IRS-1 defines a unique signal transduction protein", Jul. 4, 1991, Nature, 352:73-77.
Süntar, et al., Comparative evaluation of traditional prescriptions from *Cichorium intybus* L. for wound healing: Stepwise isolation of an active component by in vivo bioassay and its mode of activity, 2012, J Ethnopharmacol, 143 (1):299-309.
Till, et al., "Crystallographic and Solution Studies of an Activation Loop Mutant of the Insulin Receptor Tyrosine Kinase: Insights into kinase mechanism", Mar. 30, 2001, J Biol Chem, 276(13):10049-10055.
TKDL Abstract No. BA3/1453, Mohammad Akmal Khan, "Nuskha-e-Kaahu Bara-e-Ziabetus", Qaraabaadeen Azam wa Akmal (19th century AD), Matba Siddiqi, Delhi I Matba Mustafai, Delhi, 1897 AD p. 273.
TKDL Abstract No. AH5/2576, Mohammad Akmal Khan, "Qurs-e-Masikul Baul Deegar", Qaraabaadeen Azam wa Akmal (19th century AD), Matba Siddiqi, Delhi I Matba Mustafai, Delhi, 1897 AD p. 582.
TKDL Abstract No. BA3/1454, Mohammad Akmal Khan, "Sheera-e-Khurfa Bara-e-Ziyabetus Harr", Qaraabaadeen Azam wa Akmal (19th century AD), Matba Siddiqi, Delhi I Matba Mustafai, Delhi, 1897 AD p. 274.
TKDL Abstract No. KU1C/13 & Mohammad Azam Khan, "Baqool Bara-e-Ziabetes", Ikseer Azam, vol. III (19th century AD), Munshi Nawal Kishore, Lucknow, 1917 AD p. 451.
TKDL Abstract No. MA3/473, Mohammad Kabiruddin, "Qurs Ziabetus", Bayaaz-e-Kabir, vol. II (Compiled), Daftar al Maseeh, Karol Bagh, New Delhi, 1938 AD p. 128-129.
TKDL Abstract No. MH1/2718, Mohammad Shareef Khan, "Dawa Bara-e -Ziabetus", Ilaaj-al-Amraaz (18th century AD), Afzal-al-Matabe, Barqi Press, Delhi, 1921 AD p. 229.
TKDL Abstract No. NG/257 & "Kursa Tabashir", Caru Cikitsa—Complied by Vaidya Gopinathaji Gupt, Published by Unjha Pharmacy, Gujarat, 4th edition 1950 p. 89.
Tousch, et al., "Chicoric acid, a new compound able to enhance insulin release and glucose uptake", Dec. 2008, Biochem Biophys Res Commun, 377:131-135. Published online Oct. 1, 2008.
Van de Venter, et al., "Antidiabetic screening and scoring of 11 plants traditionally used in South Africa", 2008, J Ethnopharmacol, 119:81-86. Published online Jun. 5, 2008.
Vaxillaire, et al., "Impact of Common Type 2 Diabetes Risk Polymorphisms in the DESIR Prospective Study", Jan. 2008, Diabetes, 57:244-254. Published online Oct. 31, 2007.
Villegas, et al., "Vegetable but Not Fruit Consumption Reduces the Risk of Type 2 Diabetes in Chinese Women", 2008, J Nutr, 138:574-580.
Vinson, et al., "Randomized, double-blind, placebo-controlled, linear dose, crossover study to evaluate the efficacy and safety of a green coffee bean extract in overweight subjects", Jan. 17, 2012, Diabetes Metab Syndr Obes, 5:21-27.
Weir, et al., "A dominant role for glucose in β cell compensation of insulin resistance", Jan. 2007, J Clin Invest, 117 (1):81-83.
Wellen, et al., "Inflammation, stress, and diabetes", May 2005, J Clin Invest, 115(5):1111-1119.
White, "Insulin Signaling in Health and Disease", Dec. 5, 2003, Science, 302:1710-1711.
White, "Regulating insulin signaling and β-cell function through IRS proteins", 2006, Can J Physiol Pharmacol, 84:725-737. Published online Sep. 20, 2006.
White, et al., "A Cascade of Tyrosine Autophosphorylation in the β-Subunit Activates the Phosphotransferase of the Insulin Receptor", Feb. 25, 1988, J Biol Chem, 263(6):2969-2980.
White, et al., "Insulin rapidly stimulates tyrosine phosphorylation of a Mr-185,000 protein in intact cells", Nov. 14, 1985, Nature, 318(6042):183-186.
White, et al., "Mutation of the Insulin Receptor at Tyrosine 960 Inhibits Signal Transmission but Does Not Affect Its Tyrosine Kinase Activity", Aug. 26, 1988, Cell, 54:641-649.
White, et al., "The Insulin Signaling System", Jan. 7, 1994, J Biol Chem, 269(1):1-4.
Withers, et al., "Disruption of IRS-2 causes type 2 diabetes in mice", Feb. 26, 1998 Nature, 391:900-904.
Wolfender, et al., "Liquid chromatography with ultraviolet absorbance-mass spectrometric detection and with nuclear magnetic resonance spectrometry: a powerful combination for the on-line structural investigation of plant metabolites", 2003, Journal of Chromatography A, 1000 2003:437-455. Published online Feb. 17, 2008.
Wu, et al., "Structural and biochemical characterization of the KRLB region in insulin receptor subsliate-2", Mar. 2008, Nat Struct Mol Biol, 15(3):251-258.
Xavier-Filho, et al., "Plant insulin or glucokinin: a conflicting issue", 2003, Braz J Plant Physiol, 15(1):67-78.
Yenush, et al., "The IRS-signalling system during insulin and cytokine action", 1997, Bio Essays, 19(5):491-500.
Zhang, et al., "Discovery of a Small Molecule Insulin Mimetic with Antidiabetic Activity in Mice", May 7, 1999, Science, 284:974-977.
Zick, "Ser/Thr Phosphorylation of IRS Proteins: A Molecular Basis for Insulin Resistance", Jan. 25, 2005, Sci STKE, 2005(268):pe4. 3 pages.

(56) References Cited

OTHER PUBLICATIONS

Chinese Patent Application No. 201480026762.7, filed Mar. 12, 2014, First Office Action and Search Report dated Oct. 18, 2018, 18 pages. Translation of Office Action provided.

Li, et al., "Study on effect of aqueous extract of *Sonchus* L for reducing blood sugar in an experimental mouse suffering from Diabetes Mellitus", 2011, Lishizhen Medicine and Materia Medica Research, 22(2)419-421. No translation provided. See translated text of Office Action dated Oct. 18, 2018 in Chinese Patent Application No. 201480026762.7 for relevance.

Adeneye et al., "Hypoglycemic and hypolipidemic effects of fresh leaf aqueous extract of Cymbopogon citratus Stapf. in rats", 2007, J Ethnopharmacol, 112:440-444. Available online Apr. 8, 2007.

Anand, et al., "Preliminary studies on antihyperglycemic effect of aqueous extract of *Brassica nigra* (L.) Koch in streptozotocin induced diabetic rats", Aug. 2007, Indian J Exp Biol, 45:696-701.

Aslan, et al., "Hypoglycemic activity and antioxidant potential of some medicinal plants traditionally used in Turkey for diabetes", 2010, Journal of Ethnopharmacology, 128:384-389. Available online Jan. 25, 2010.

Broadhurst, et al., "Insulin-like Biological Activity of Culinary and Medicinal Plant Aqueous Extracts in Vitro", 2000, J. Agric. Food Chem., 48(3):849-852. Published online Mar. 2, 2000.

Brunton et al., editors, "Goodman & Gilman's The Pharmacological Basis of Therapeutics, 12th Edition", 2011, McGraw-Hill Medical, New York, New York, Cover, title page, publishing information page and pp. 45-46.

Hu, et al., "Research Progress of Chicory Polysaccharide", Dec. 31, 2013, Prataculture & Animal Husbandry, No. 2, pp. 44-48. English Abstract and machine translation provided.

Mahmoud, "Antidiabetic and Antioxidant Effects of Parsley Extract (*Petroselium crispum* on Diabetic Rats", 2011, Isotope and Radiation Research, 43(2):341-357. Abstract only.

Mohamed, et al., "The Antihyperglycaemic Effect of the Aqueous Extract of Origanium vulgare Leaves in Streptozotocin-Induced Diabetic Rats", Mar. 2013, Jordan Journal of Biological Sciences, 6(1):31-38.

Neef et al., "Hypoglycaemic Activity of Selected European Plants", Jan. 1, 1995, Phytotherapy Research, 9 (1):45-48.

Park, et al., "Extracts of Rehmanniae radix, Ginseng radix and Scutellariae radix improve glucose-stimulated insulin secretion and β-cell proliferation through IRS2 induction", 2008, Genes & Nutrition, 2:347-351. Published online Nov. 20, 2007.

Roman-Ramos, et al., "Experimental study of the hypoglycemic effect of some antidiabetic plants", 1991, Archivos de Investigacion Medica, 22(1):87-93.

Shetty, Akhila K., et al., "Effect of the insulin plant (*Costus igneus*) leaves on dexamethasone-induced hyperglycemia", Apr.-Jun. 2010, International Journal of Ayurveda Research, 1(2):100-102.

Weinoehrl, et al., "Comparative Evaluation of Two Different *Artemisia dracunculus* L. Cultivars for Blood Sugar Lowering Effects in Rats", Apr. 2012, Phytotherapy Research, 26:625-629. Published online Sep. 23, 2011.

Weinöhrl, "Screening of Various Extracts of *Artemisia dracunculus* L. for Antidiabetic Activity in Rats, Diploma Thesis", Aug. 2010, University of Vienna, Austria, 67 pages. Available online at http://othes.univie.ac.at/10845/.

Zhao, et al., "Distribution and comprehensive development and utilization of wild tarragon in Xinjiang", Dec. 31, 2007, Northern Horticulture, No. 5, pp. 60-63. English Abstract and machine translation provided.

A.

B.

A.

B.

PLANT EXTRACTS WITH ANTI-DIABETIC AND OTHER USEFUL ACTIVITIES

CROSS-REFERENCE TO RELATED APPLICATIONS

This application is the § 371 U.S. National Stage of International Application No. PCT/US2018/032273, filed May 11, 2018, which claims the benefit of and priority to U.S. Provisional Patent Application No. 62/505,494, filed on May 12, 2017, the disclosures of which are expressly incorporated by reference herein in their entireties.

FIELD OF THE INVENTION

This invention relates to plant extracts containing nutritionally beneficial or medicinally active compounds. Some of these extracts, or the purified compounds contained therein, may be used for the nutritional support, prevention, treatment, or possible cure of various metabolic and other diseases and disorders in human beings and animals, including type 1 and type 2 diabetes, by regulating insulin signaling. This regulatory effect may include modulations of the levels and/or activity of the Insulin Receptor (IR), the Insulin-like Growth Factor (IGF) Receptor, and/or the Insulin Receptor Substrate (IRS) proteins in cells and tissues in the body. A primary focus is directed toward the IRS proteins. Two members of the IRS family of proteins, IRS1 and IRS2, are part of the insulin or insulin-like growth factor signaling pathways, but also mediate signals through other growth factors and cytokines, including IFN-γ, IL-2, IL-4, IL-7, IL-9, IL-13 or IL-15, growth hormone, prolactin, or leptin. IRS1 or IRS2 functional activities also integrate signals emanating from proinflammatory cytokines, including TNF-α, IL-6, IL-1β and related factors. In general proinflammatory cytokines inhibit IRS1/IRS2 signaling which contributes to insulin resistance syndromes.

BACKGROUND OF THE INVENTION

Diabetes mellitus is a complex and life threatening disease that has been known for more than 2000 years. It occurs in mammals as diverse as monkeys, dogs, rats, mice and human beings. The discovery and purification of insulin in 1921 by Banting and Best and its subsequent therapeutic use in people was a landmark advance in medical science and provided a partial treatment for diabetes that is still in widespread use today. Insulin levels are ordinarily adjusted by the body on a moment to moment basis to keep the blood sugar level within a narrow physiological range. In the diabetic patient, however, periodic insulin injections can only approximate the normal state because the cellular response to insulin in organs and tissues such as liver, muscle and fat is in many cases is also reduced. Consequently, for these and other reasons which will be discussed in detail below, life threatening complications still occur during the lifetime of treated diabetic patients, especially in the case of type 2 (adult-onset) diabetes. (1)

Diabetes arises from various causes, including autoimmune-mediated β-cell destruction (type 1 diabetes); insufficient β-cell insulin secretory capacity to compensate for peripheral insulin resistance (type 2 diabetes); and impaired glucose sensing or insulin secretion (Maturity Onset Diabetes of Youth; MODY) (1). Type 1 Diabetes is genetically complex and caused by circulating auto-antibodies against a variety of islet antigens. Insulin is thought to be one of the principle autoantigens in the pathogenesis of type 1 diabetes, but other antigens deserve attention (2). Since new β-cell formation occurs slowly while type 1 diabetes progresses, it might be necessary to treat the disease by accelerating the rate of β-cell regeneration while attenuating the autoimmune response (3).

Type 2 diabetes is the most prevalent form of diabetes. While it typically manifests at middle age, type 2 diabetes in the developed world is becoming more common in children and adolescents. Physiologic stress—the response to trauma, inflammation, or excess nutrients—promotes type 2 diabetes by activating pathways that impair the post-receptor response to insulin in various tissues (1). Genetic variation also modifies the response to environmental and nutritional factors that promote type 2 diabetes. In a few informative cases, mutations in the insulin receptor or AKT2 explain severe forms of insulin resistance (4). However, common forms of type 2 diabetes are associated with multiple gene variants with modest effects upon insulin action—including peroxisome proliferator-activated receptor gamma (PPARG), peroxisome proliferator activated receptor, gamma, coactivator 1 alpha (PPARGC1A), inward rectifying K+-channel Kir6.2 (KCNJ11), calpain-10 (CAPN10), transcription factor 7-like 2 (TCF7L2), adiponectin (ADIPOQ), adiponectin receptor 2 (ADIPOR2), hepatocyte nuclear factor 4 alpha (HNF4A), uncoupling protein-2, (UCP2), sterol regulatory element binding transcription factor 1 (SREBF1), or high plasma interleukin-6 concentrations (5). Although the effect of each gene is small, these discoveries provide important clues to the pathogenesis of type 2 diabetes.

Regardless of the underlying etiology, dysregulated insulin signaling exacerbated by chronic hyperglycemia and compensatory hyperinsulinemia promotes a cohort of acute and chronic sequela (6). Untreated diabetes progresses to ketoacidosis (most frequent in type 1 diabetes) or hyperglycemic osmotic stress (most frequent in type 2 diabetes), which are immediate causes of morbidity and mortality. In the long term, diabetes is associated with numerous chronic life threatening complications. Due to the marked increase in cerebrovascular disease that occurs in diabetics, the incidence of stroke is as much as three-fold higher than in the non-diabetic population. Similarly, cardiovascular diseases such as peripheral vascular disease, congestive heart failure, coronary artery disease and myocardial infarction are uniformly increased in diabetics as a result of the synergistic effects of hyperglycemia with other cardiovascular risk factors. Furthermore, the combined effects of reduced cardiovascular function and systemic oxidative stress result in damage to capillary endothelial cells in the retina (leading to blindness), mesangial cells of the renal glomerulus causing renal failure, and peripheral nerves resulting in neuropathies causing pain and numbness in the extremities (7).

Diabetes is also associated with age-related degeneration in the central nervous system. Humans beyond 85-90 years of age display less insulin resistance than expected—and centenarians are surprisingly insulin sensitive (8). Compounds that promote peripheral insulin sensitivity and reduce the concentration of circulating insulin required to maintain normal glucose homeostasis provide an ideal treatment of glucose intolerance and its progression to life-threatening diabetes.

Insulin, Insulin-Like Growth Factors, and Receptors

Mammals produce three insulin-like peptides—insulin, insulin-like growth factor-1 (IGF-1) and insulin like growth factor-2 (IGF-2)—which activate five homologous insulin-like receptor tyrosine kinases encoded by the insulin receptor (IR) gene and the insulin-like growth factor-1 receptor (IGF1R) gene (FIG. 1A/B). Insulin is produced in pancreatic β-cells in response to circulating glucose concentrations, whereas endocrine IGF-1 is largely secreted from hepatocytes stimulated by nutrients and growth hormone; IGF-1 and IGF-2 are also produced locally in many tissues and cells, including the central nervous system (9). IGF1 can work coordinately with insulin to regulate nutrient homeostasis, insulin sensitivity and pancreatic β-cell function (9). The insulin receptor and IGF receptor genes encode homologous precursors that form covalently linked dimers that are cleaved by proteolysis to generate a tetramer with two extracellular α-subunits and two transmembrane β-subunits. The extracellular α-subunits create the ligand-binding domain that regulates the activity of the tyrosine kinase on the intracellular portion of the transmembrane β-subunits (10).

High affinity ligand binding induces structural transitions in the catalytic domain of the β-subunit that promote phosphorylation of three tyrosine residues in the kinase regulatory loop (IRa)-Tyr1158, Tyr1162 and Tyr1163 (11). Autophosphorylation releases the regulatory loop from its inhibitory position, which opens the catalytic sites to phosphorylate other proteins (12). The phosphorylated regulatory loop also interacts with other signaling proteins that modulate kinase activity, including Grb10, Grb14, APS and SH2B (13). A fourth tyrosine residue within an NPEY-motif located outside the kinase domain and near the plasma membrane (Tyr960 in IRb; Tyr972 in IRa; Tyr950 in IGF1R) is also phosphorylated, which recruits insulin receptor substrates (IRS-proteins) for tyrosine phosphorylation by the activated receptor kinase (14).

Insulin Receptor Substrates

Cell-based and mouse-based experiments show that most if not all insulin signals are produced or modulated through tyrosine phosphorylation of IRS1, IRS2 or its homologs; or other scaffold proteins including SHC, CBL, APS and SH2B, GAB1, GAB2, DOCK1, and DOCK2 (15). Although the role of each of these substrates merits attention, work with transgenic mice suggests that many insulin responses—especially those that are associated with somatic growth and nutrient homeostasis—are mediated through IRS1 or IRS2 (1).

The first member of the insulin receptor substrate family of proteins was discovered in 1985, and subsequent research efforts revealed the existence of related IRS family members as well as the signaling pathways to which the IRS proteins are linked. After the discovery that the insulin receptor (IR) possessed a tyrosine kinase enzyme activity, many groups searched for insulin receptor substrates that might regulate downstream signaling from the receptor. The first evidence for the existence of an actual target protein for the insulin receptor, subsequently named an Insulin Receptor Substrate, or "IRS" protein, resulted from the use of phosphotyrosine antibody immunoprecipitates which surprisingly revealed a 185-kDa phosphoprotein (pp185) in insulin-stimulated hepatoma cells (16). Purification and molecular cloning of pp185 revealed one of the first signaling scaffolds as well as the first Insulin Receptor Substrate protein (IRS1) (17,18). IRS1 was determined to be biologically important because it was phosphorylated immediately after insulin stimulation, and catalytically active insulin receptor mutants that failed to phosphorylate IRS1 were biologically inactive.

Several experiments suggested that other related proteins might exist which led to the purification and cloning of Insulin Receptor Substrate 2 (IRS2), a second member of the IRS family (19,20).

Experiments in transgenic mice revealed involvement of IRS1 and IRS2 in promoting somatic growth and nutrient homeostasis. Without IRS1, mice are 50% smaller than normal from birth until they die at 2 years of age. Mice without IRS1 have less body fat and are glucose intolerant. In mice, IRS2 is important for peripheral insulin action, as mice lacking IRS2 display glucose intolerance and hyperlipidemia.

Disruption of the IRS2 gene in mice using standard gene knockout approaches results in diabetes that develops between 8-12 weeks of age. Pancreatic β-cells are lost from these mice as they age, and genes that are important for β-cell function are dysregulated in mice lacking IRS2.

The IRS-proteins are adapter molecules that link the insulin-like receptors to common downstream signaling cascades (FIG. 1A/B). Four IRS-protein genes have been identified in rodents, but only three of these genes (IRS1, IRS2 and IRS4) are expressed in humans. IRS1 and IRS2 are broadly expressed in mammalian tissues, whereas IRS4 is largely restricted to the hypothalamus and at low levels in a few other tissues. Each of these proteins is targeted to the activated insulin-like receptors through an NH2-terminal pleckstrin homology (PH) domain. The PTB domain binds specifically to the phosphorylated NPEY-motif in the activated receptor kinases (1). The PH domain also promotes the interaction between IRS proteins and the IR, but the mechanism is poorly understood. The PH domain in the IRS-protein plays a specific role as it can be interchanged among the IRS-proteins without noticeable loss of bioactivity, but heterologous PH domains inhibit IRS1 function when substituted for the normal PH domain (21). In addition to the PH and PTB domains, IRS2 also utilizes another mechanism to interact with the activated insulin receptor (22).

IRS→PI3K→AKT Cascade

One of the best studied insulin-like signaling cascades involves the production of PI-3,4,5-P3 by the phosphatidylinositol 3-kinase (PI 3-kinase). The type 1 PI 3-kinase is composed of a regulatory subunit that contains 2 src-homology-2 (SH2) domains and a catalytic subunit that is inhibited by the regulatory subunit until its SH2 domains are occupied by phosphorylated tyrosine residues in the IRS-proteins (23). PI-3,4,5-P3 recruits the Ser/Thr-kinases PDK1 and AKT (also known as PKB) to the plasma membrane where AKT is activated by PDK1-mediated phosphorylation (FIG. 1A/B). AKT phosphorylates many proteins that play a central role in cell survival, growth, proliferation, angiogenesis, metabolism, and migration (24). Phosphorylation of several genuine AKT substrates is especially relevant to insulin-like signaling: GSK3α/β (blocks inhibition of glycogen synthase), AS160 (promotes GLUT4 translocation), the BAD•BCL2 heterodimer (inhibits apoptosis), the FOXO transcription factors (regulates gene expression), p21CIP1 and p27KIP1 (blocks cell cycle inhibition), eNOS (stimulates NO synthesis and vasodilatation), and PDE3b (hydrolyzes cAMP) (FIG. 1A/B). AKT also phosphorylates tuberin (TSC2), which inhibits its GAP activity toward the small G-protein RHEB promoting the accumulation of the RHEB•GTP complex that activates mTOR (24): This pathway provides a direct link between insulin signaling and protein synthesis that is needed for cell growth (FIG. 1A/B).

The role of IRS-proteins in the PI3K→AKT signaling cascade is validated by a wide array of cell-based and mouse-based experiments. Although IRS1 was originally purified and cloned from rat hepatocytes, the principle role of IRS1 and IRS2 during insulin signaling in hepatocytes in vivo was verified only recently (25). The simplest experiments employ an intraperitoneal injection of insulin into ordinary mice, or mice lacking hepatic IRS1 and IRS2. In ordinary mice, insulin rapidly stimulates Akt phosphorylation, and the phosphorylation of its downstream substrates Foxo1 and Gsk3α/β. Both IRS1 and IRS2 must be deleted to uncouple the insulin receptor from the PI3K→AKT cascade (25). These results confirm the shared but absolute requirement for IRS1 or IRS2 for the hepatic insulin signaling.

Transcriptional Regulation of IRS2

The regulation of IRS-protein signaling is an important way to coordinate the intensity and duration of the insulin response among various tissues, but failure of these mechanisms can cause insulin resistance. Transcription of the IRS1 gene is generally stable. By contrast, the production of IRS2 is regulated by multiple nutrient-sensitive transcription factors, including cAMP response element binding protein (CREB) and its binding partner CRTC2, forkhead box O1 (FOXO1), transcription factor E3 (TFE3), and sterol regulatory element binding/factor-1c (SREBF-1c) (26,27). Interestingly, the CREB/CRTC2 transcriptional complex—which binds to cAMP response elements (CRE)—has opposite effects upon IRS2 expression in β-cells and liver. After a meal, the production of ATP from glucose oxidation depolarizes β-cells, which promotes both Ca2+ influx and cAMP production that has many important effects, including the activation of CREB/CRTC2 (26). Thus glucose is coupled directly to IRS2 expression in β-cells, which stimulates β-cell growth and compensatory insulin secretion. By contrast, CREB/CRTC2 promotes IRS2 expression in the fasting liver, which can inhibit the gluconeogenic program by augmenting the basal insulin response.

In addition to cAMP response elements the promoter region of the IRS2 gene includes elements that bind FOXO family members, an E-box that binds TFE3, and a sterol response element (SRE) recognized by SREBF-1c (27). FOXO1 links the PI3K-AKT cascade to the expression of genes important in cell growth, survival, and metabolism. In liver, IRS1 and IRS2 promote the phosphorylation, nuclear export and degradation of FOXO1, which reduces IRS2 expression. Moreover, SREBF-1c concentrations increase during nutrient excess and chronic insulin stimulation, which inhibits FOXO1-mediated IRS2 expression (28). An imbalance in this reciprocal regulation appears to contribute to pathophysiological effects of over-nutrition leading to the development of the metabolic syndrome and diabetes. Thus, compounds that promote IRS2 signaling are expected to have a strong normalizing effect upon hepatic insulin action, especially during nutrient excess.

Insulin Resistance and the Dysregulation of IRS-Protein Signaling.

Insulin resistance is a common pathological state that is associated with many health disorders—obesity, hypertension, chronic infection, dysregulated female reproduction, and kidney and cardiovascular diseases (1). Over the past 15 years, mouse-based experiments have revealed how mutations in genes that mediate the insulin signal, modulate the insulin signal, or respond to the insulin signal contribute to insulin resistance and diabetes. Whereas genetic mutations are obvious sources of life-long insulin resistance, they are usually associated with rare metabolic disorders. Environmental, physiological, and immunological stress causes insulin resistance through heterologous signaling cascades coordinated by complex genetic backgrounds (1).

Obesity is essentially associated with peripheral insulin resistance. Recent studies reveal a variety of factors secreted from adipose tissue that inhibit insulin signaling—FFAs, tumor necrosis factor-alpha (TNFα), and resistin; or factors that promote insulin signaling-adipocyte complement-related protein of 30 kDa (adiponectin) and leptin. Each one of these factors has specific effects upon gene expression patterns that can alter the response of a cell to insulin. However, the effect of these factors upon the expression or function of the IRS-proteins could contribute to the mechanism for insulin resistance (29). Signaling cascades activated during acute trauma or chronic metabolic or inflammatory stress dysregulate IRS-proteins through various mechanisms, including phosphatase-mediated dephosphorylation, proteasome-mediated degradation, and Ser/Thr-phosphorylation. Dysregulation of IRS-protein function also provides a plausible framework to understand the loss of compensatory β-cell function while peripheral insulin resistance emerges (30).

Experiments with TNFα reveal one of the first mechanisms linking inflammatory cytokines to insulin resistance (31). TNFα activates the NH2-terminal JUN kinase (JNK), which phosphorylates IRS1 on serine residues that inhibit the activation of the PI 3-kinase/Akt pathway in response to insulin. JNK-mediated phosphorylation of IRS1 may also mediate the effects of cellular stress, including endoplasmic reticulum stress. Insulin itself promotes serine phosphorylation of IRS1 through activation of the PI 3-kinase, revealing feedback regulation that might be mediated by many kinases—AKT, PKCζ, IKKβ, JNK, mTOR and S6K1 (29).

The Central Role of IRS2 Signaling in Pancreatic β-Cells and Insulin Resistance.

Mice lacking the gene for Irs1 or Irs2 are insulin resistant, with impaired peripheral glucose utilization. Both types of knockout mice display metabolic dysregulation, but only the Irs2−/− mice develop diabetes between 8-12 weeks of age owing to a near complete loss of pancreatic β-cells (32). This result positions the insulin-like signaling cascade through IRS2 at the center of β-cell function.

Many factors are required for proper β-cell function, including the homeodomain transcription factor Pdx1. Pdx1 regulates downstream genes needed for β-cell growth and function, and mutations in PDX1 cause autosomal forms of early-onset diabetes in people (MODY). Pdx1 is reduced in Irs2−/− islets and Pdx1 haploinsufficiency further diminishes the function of β-cells lacking Irs2. Glucose and glucagon-like peptide-1 have strong effects upon β-cell growth, which depend upon the Irs2 signaling cascade (FIG. 1B). In β-cells, Irs2 is up regulated by cAMP and Ca2+ agonists—including glucose and glucagon-like peptide-1 (GLP1)—which activate cAMP responsive element binding protein (CREB) and the CREB-regulated transcription co-activator 2 (CRTC22) (34). While many cAMP mediated pathways oppose the action of insulin, the up regulation of IRS2 by glucose and GLP1 reveals an unexpected intersection of these important signals (FIG. 1B). Thus, hyperglycemia resulting from the daily consumption of high caloric food promotes β-cell growth, at least in part by increasing IRS2 expression (34). These results suggest that the Irs2-branch of the insulin-like signaling cascade is the "ordinary gatekeeper" for β-cell plasticity and function. Thus compounds that promote IRS2 signaling might have beneficial effects upon beta cell growth, survival and function.

Peripheral insulin resistance contributes to type 2 diabetes, but β-cell failure is an essential feature of all types of diabetes. β-cells frequently fail to compensate for insulin resistance, at least in part because the IRS2-branch of the insulin and IGF signaling cascade which mediates insulin signaling in target tissues also is essential for β-cell growth, function and survival (32).

Because insulin resistance is a cause of metabolic dysregulation and diabetes, understanding its molecular basis is an important goal. Genetic mutations are obvious sources of life-long insulin resistance, but they are associated with rare metabolic disorders and thus difficult to identify in the general population. Inflammation is associated with insulin resistance and provides a framework to understand how diet, acute or chronic stress, and obesity might cause insulin resistance.

Ubiquitin-mediated degradation of IRS-proteins also promotes insulin resistance (FIG. 1A/B). IL6 secreted from leukocytes and adipocytes increases expression of SOCS1 and SOCS3, known for the ability to suppress cytokine signaling. Another function of SOCS1 and SOCS3 is to recruit an elongin BC-based ubiquitin ligase into the IRS-protein complex to mediate ubiquitinylation. Thus, ubiquitin-mediated degradation of IRS-proteins might be a general mechanism of cytokine-induced insulin resistance that contributes to diabetes or β-cell failure (35).

The activity of protein or lipid phosphatases, including PTP1B, SHIP2 or pTEN modulates insulin sensitivity (FIG. 1). Disruption of each of these genes in mice increases insulin sensitivity, suggesting that each might be a target for inhibitor design. PTP1B resides in the endoplasmic reticulum where it dephosphorylates the insulin receptor during internalization and recycling to the plasma membrane (36). This specialized mechanism appears to limit unwanted side effects associated with inhibition of phosphatases, including unregulated cell growth.

SUMMARY OF THE INVENTION

The insulin receptor substrate (IRS) family of proteins that function immediately downstream of the insulin receptor or insulin like growth factor receptors is of central importance in mediating the effects of insulin on responsive cells. In particular, upregulation of the level or functional activity of IRS2 in humans may result in a therapeutically effective chronic treatment as well as a nutritionally beneficial or supportive effect for patients suffering from diabetes, especially the adult onset (type 2) form of the disease, as well as for other disorders in which IRS protein function is insufficient, abnormal or absent altogether. Further, IRS1 and IRS2 are of central importance in mediating signaling through the insulin like growth factor signaling pathway, and signaling by other growth factors and cytokines as well.

Compounds of the invention may be identified using 32D cells expressing IRS2. Such cells may be created using standard methodology (20). Applicant's have previously created and described a sophisticated target protein specific cell-based assay system capable of identifying IRS2 branch activators of the insulin mediated signal transduction cascade (38). This system is comprised of both Control and Test cells derived from the 32D myeloid progenitor cell line. For the present invention, Applicants designed a cell-based assay system using an IRS2 overproducing histidinol-resistant Test cell line as well as an appropriate his-resistant Control cell line harboring the expression vector only. Under appropriate cultural conditions, the IRS2 overproducing 32D cells become exquisitely sensitive to activation by insulin. Compounds of the present invention will have a more pronounced effect on the Test cells than on the Control cells, and this effect is quantitated and used to determine the ability of a sample to mimic the effects of insulin as expressed in percentage terms relative to the maximum effect observed following insulin treatment.

Representative assay results (shown in Tables 1-2 and FIG. 5) utilize a 96 well plate format and involve plating Control and Test cells at 25,000 cells per well at time zero. The cells are cultured in IL-3-free medium, and treated for 72 hours with and without 50 nM insulin. Whereas the IRS2-overproducing 32D cell lines become IL-3 independent for the 72 hour duration of the assay (See FIG. 5), the Control cells remain absolutely IL-3 dependent and exhibit essentially no cell growth (data not shown). As a result, the assay developed is highly sensitive to compounds (such as insulin) that are capable of activating the IRS2 dependent growth control cascade in IRS2 overproducing 32D cells. Furthermore, potential false positive growth stimulating substances, as emulated by the results of treatment of the cells with IL3, will score positively on the Control cell line as well, and are thus easily eliminated from further consideration and work-up.

This system was utilized to conduct a high throughput screen consisting of more than 100,000 synthetic and natural product derived compounds in search of agents capable of activating the IRS2 signal transduction cascade. A subset of these compounds included extracts derived from a variety of plant species, some of which included edible species. The latter compounds and extracts were screened because Applicants reasoned that compounds derived from edible plants might also contain compounds that are capable of emulating the biological effects of insulin in an IRS2 dependent manner. If such compounds existed within the subset of edible plants contained within the broader plant kingdom, they would provide a basis for understanding at the molecular level why certain diets, such as the Mediterranean diet, have been shown to be associated with a reduced incidence of diabetes, heart disease, and hypertension, leading to corresponding improvements in lifespan and quality of life (40-45, 52).

Some publications have proposed the hypothesis that the benefits of such diets result from a lack of deleterious components present in them, including high fat foods, processed foods, refined sugar, artificial sweeteners and the like. Others have suggested the possibly that protective components such as general antioxidants, or essential nutritional components such as vitamins, or minerals, are the reason why certain diets are beneficial to health and well-being (40-45, 52). Applicants reasoned to the contrary that diets associated with good health and well-being might actually contain pharmacologically active components that synergize with or are otherwise beneficial to, normal cellular functioning in human beings and other mammals. By pharmacologically active, we mean that such active components bind to specific sites on proteins, nucleic acids, or other discrete cellular binding sites and exert pharmacological effects. Remarkably, this theory is demonstrated herein to be true, insofar as these efforts by the Applicants have led to the finding that plants derived from selected species, including: *Cichorium endivia*, var. latifolium; *Lactuca sativa*, var. longifolia; *Lactuca sativa*, var. crispa (See Tables 1 and 2), and others, contain one or more compounds detectable within extracts derived from said species that are capable of substantially activating the IRS2 branch of the insulin mediated signal transduction cascade as determined by the IRS2 target protein specific cell-based assay system described above and previously (38,39). Such compounds may be extracted from the aforementioned plant using an aqueous solvent system, as will be described in detail below. One of skill in the art may utilize alternative extraction methods including, but not limited to, the use of organic or inorganic solvents, and/or supercritical fluid extraction using, for example, carbon dioxide.

Tables 1 and 2 show the results obtained with a variety of distinct genera and species of edible plants that Applicants' have discovered possess the desired activity. They are ranked according to their ability to stimulate growth of the IRS2-expressing Test cells as normalized to Insulin, with the response elicited by 50 nM Insulin treatment being defined as 100% (Table 1). The activities listed in Table 1 are among the highest that were obtained from numerous experiments. Considerable variations in activity from lot to lot of plant material may be expected depending upon the time of year that the plant was grown and harvested, the degree of freshness of the plant, the soil and climate conditions in which it was propagated, and so on.

Figure 1A:
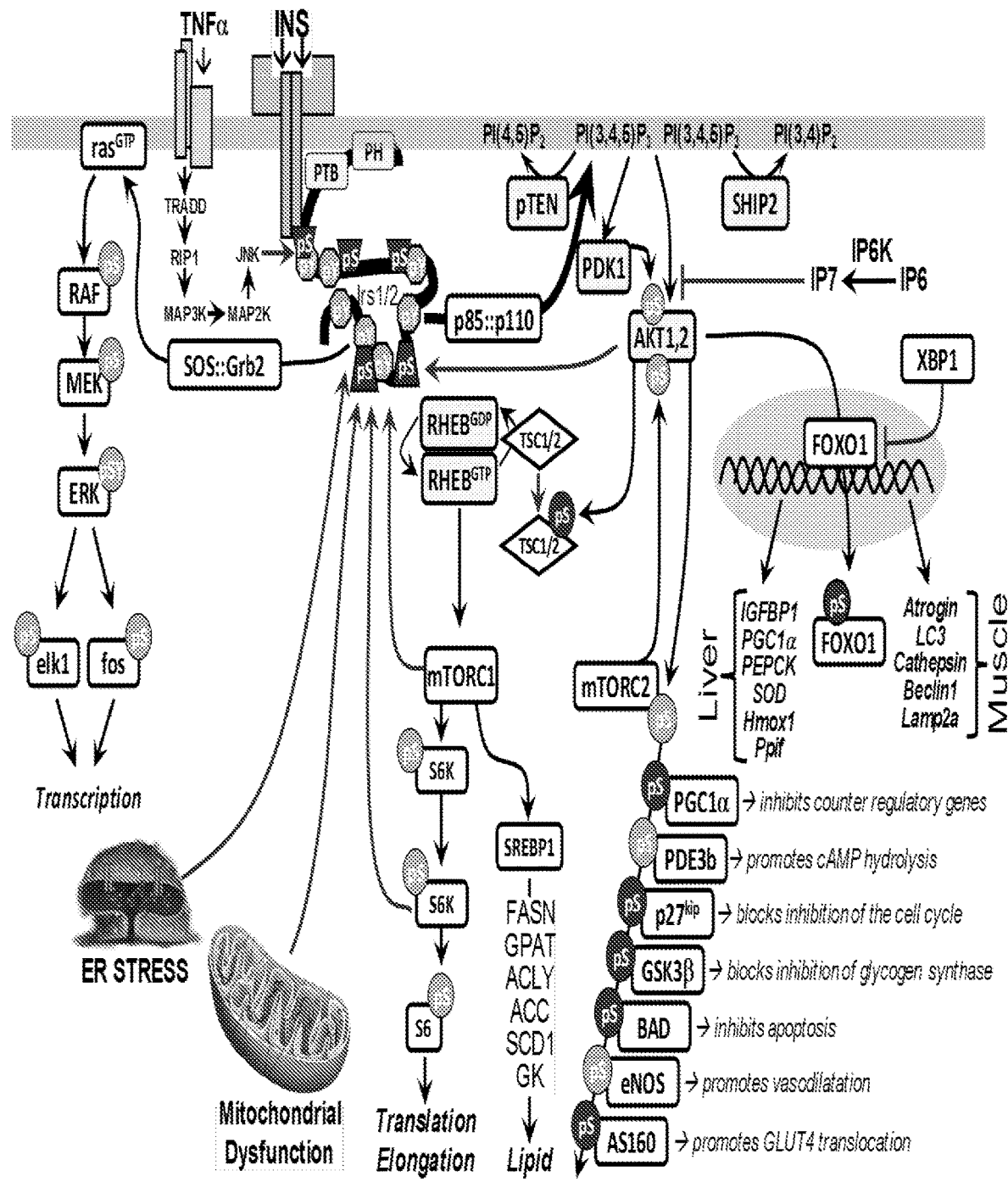
FIG. 1A and FIG. 1B depict components of the IRS signaling cascade in muscle and liver cells (FIG. 1A) and pancreatic beta cells (FIG. 1B), respectively. There are two main limbs that propagate the signal generated through the IRS-proteins: the PI 3-kinase and the Grb2/Sos→ras cascade. Activation of the receptors for insulin and IGF-1 results in tyrosine phosphorylation of the IRS-proteins, which bind PI 3-kinase and Grb2/SOS. The GRB2/SOS complex promotes GDP/GTP exchange on p21ras, which activates the ras→raf→MEK→ERK1/2 cascade. The activated ERK stimulates transcriptional activity by direct phosphorylation of elk1 and by phosphorylation of fos through p90rsk. The activation of PI 3-kinase by IRS-protein recruitment produces PI 3,4P2 and PI 3,4,5P3 (antagonized by the action of PTEN or SHIP2), which recruit PDK1 and AKT to the plasma membrane, where AKT is activated by PDK- and mTOR-mediated phosphorylation. The mTOR kinase is activated by RhebGTP, which accumulates upon inhibition of the GAP activity of the TSC1::TSC2 complex by PKB-mediated phosphorylation. The p70s6k is primed through mTOR-mediated phosphorylation for activation by PDK1. AKT phosphorylates many cellular proteins to inactivating PGC1α, p21$^{kip}$, GSK3β, BAD and AS160, or activate PDE3β and eNOS. The AKT-mediated phosphorylation of the forkhead proteins results in their sequestration in the cytoplasm, which inhibits their influence upon transcriptional activity. Insulin stimulates protein synthesis by altering the intrinsic activity or binding properties of key translation initiation and elongation factors (eIFs and eEFs, respectively) as well as critical ribosomal proteins. This occurs via phosphorylation and/or sequestration of repressive factors into inactive complexes. Components of the translational machinery that are targets of insulin regulation include eIF2B, eIF4E, eEF1, eEF2 and the S6 ribosomal protein (4-6). TNFα activates JNK which can phosphorylate IRS1 inhibiting its interaction with the insulin receptor and subsequent tyrosine phosphorylation. IRS2 expression is promoted by nuclear FOXO, which increases IRS2 expression during fasting conditions. CREB:TORC2 complex also promotes IRS2 expression especially in β-cells, placing IRS2 under the control of glucose and GLP1.
Figure 1B:
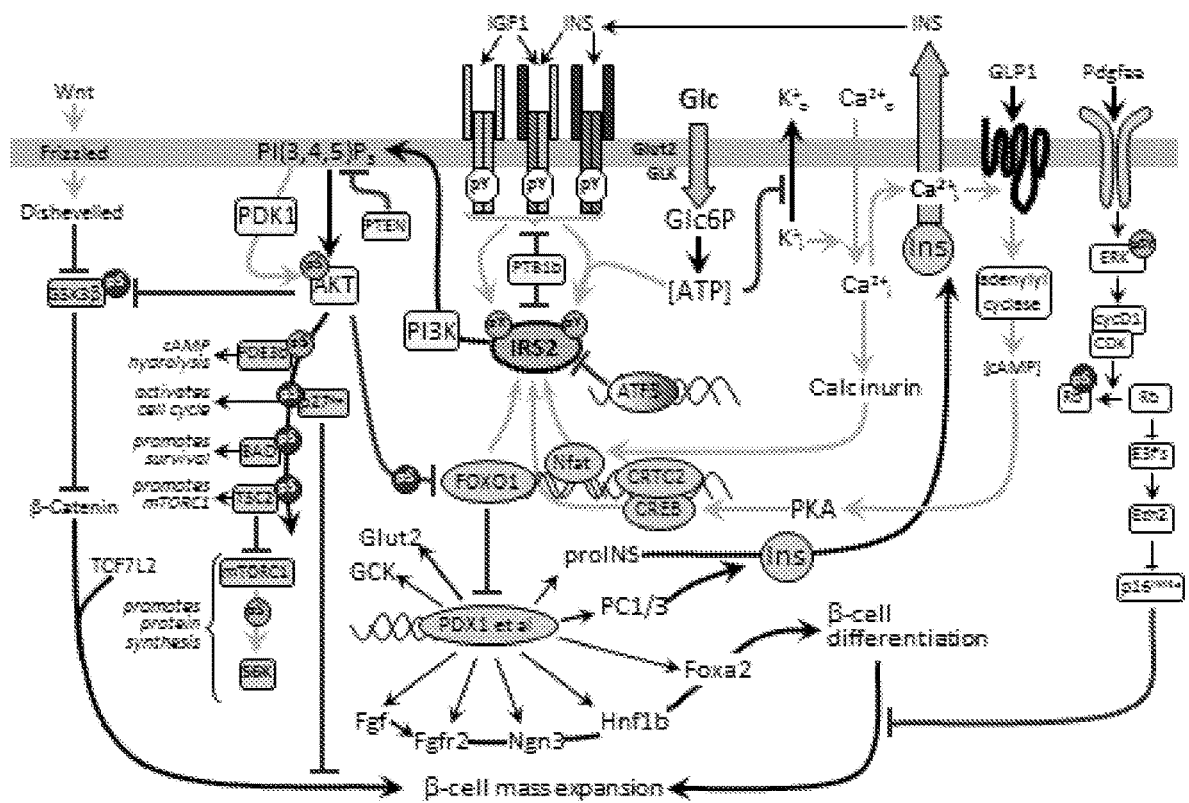
Figure 2:
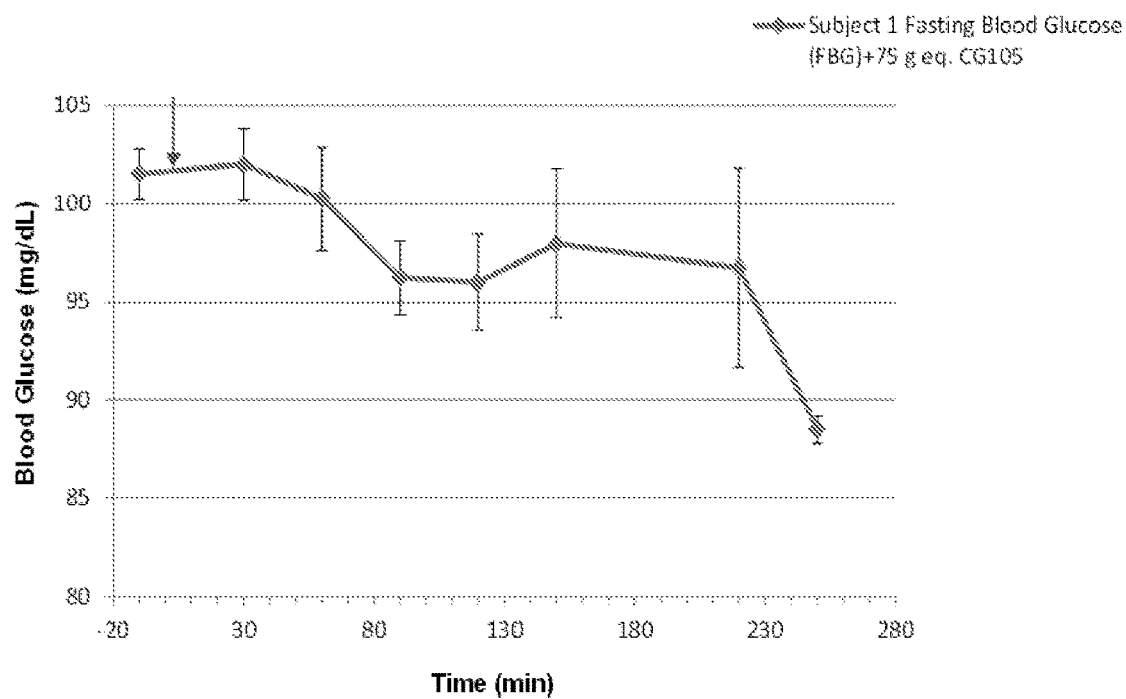
Figure 2:
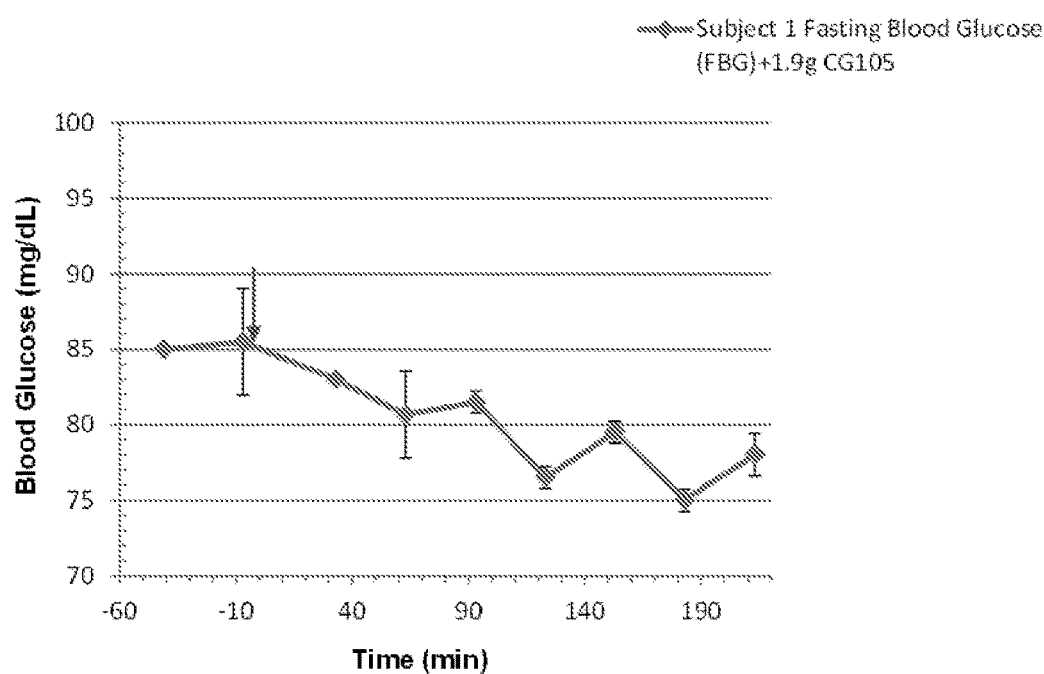
Figure 3:
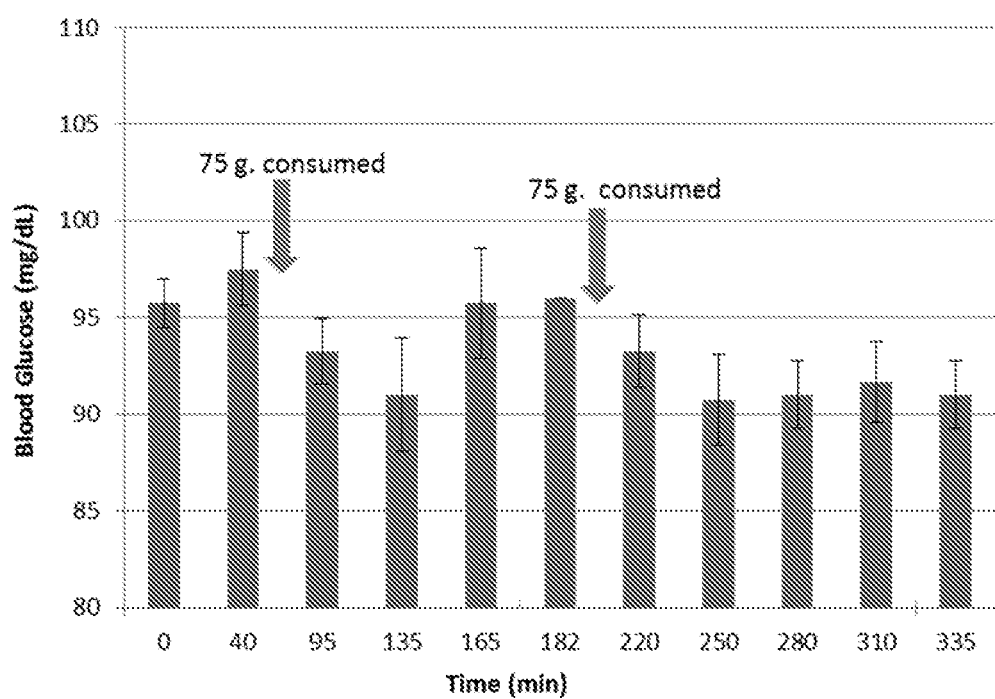
Figure 4:
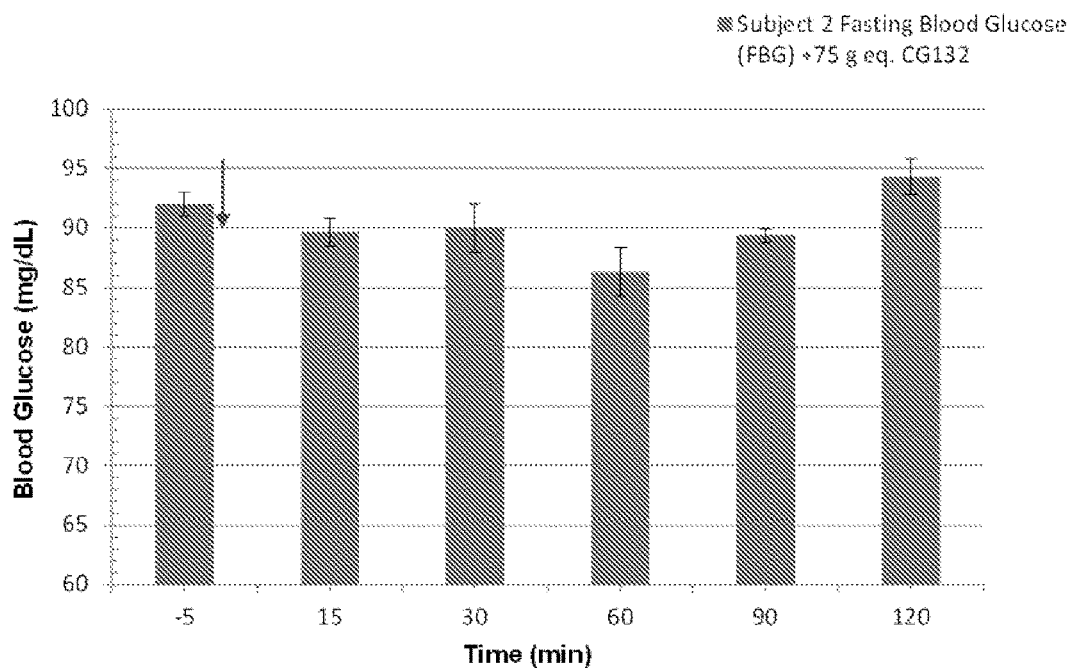
Figure 4:
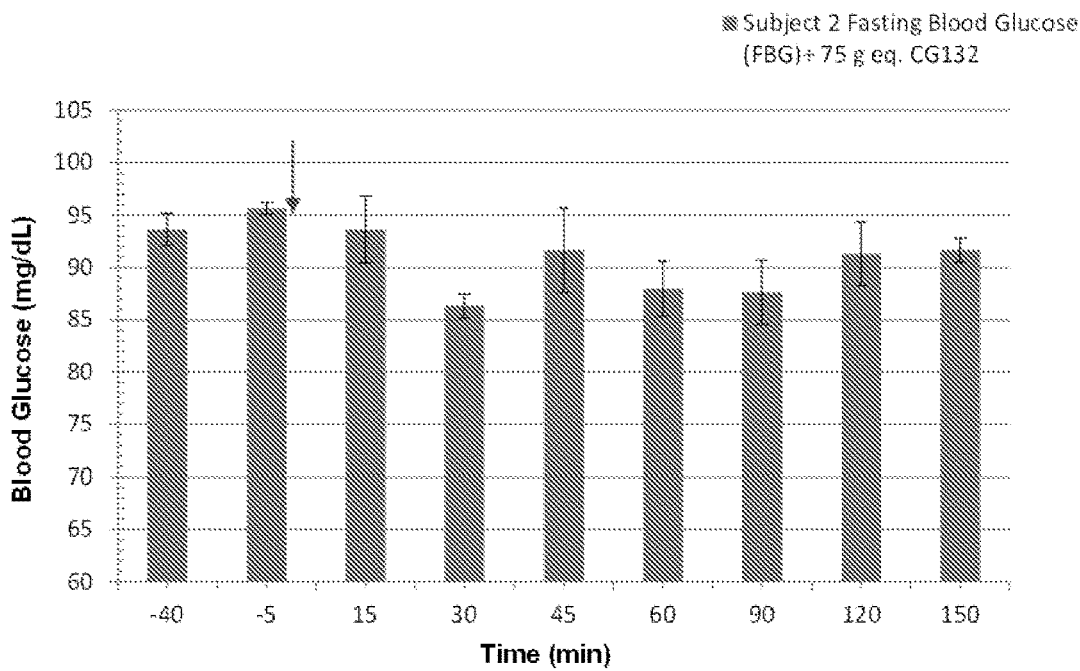

FIG. 2, FIG. 3 and FIG. 4 show the ability of certain extracts to lower fasting blood glucose in normal (non-diabetic) individuals. Either 75 grams of fresh, raw leaf obtained from a local market, or the indicated amount of lyophilized aqueous extract prepared as described herein were consumed as indicated: FIG. 2 and FIG. 3: CG-105; FIG. 4: CG-132. Blood glucose measurements were determined using a hand-held portable glucose monitor (Abbott Freestyle Freedom Lite). The glucose monitor and the disposable test strips were obtained from a local pharmacy.

Figure 5:
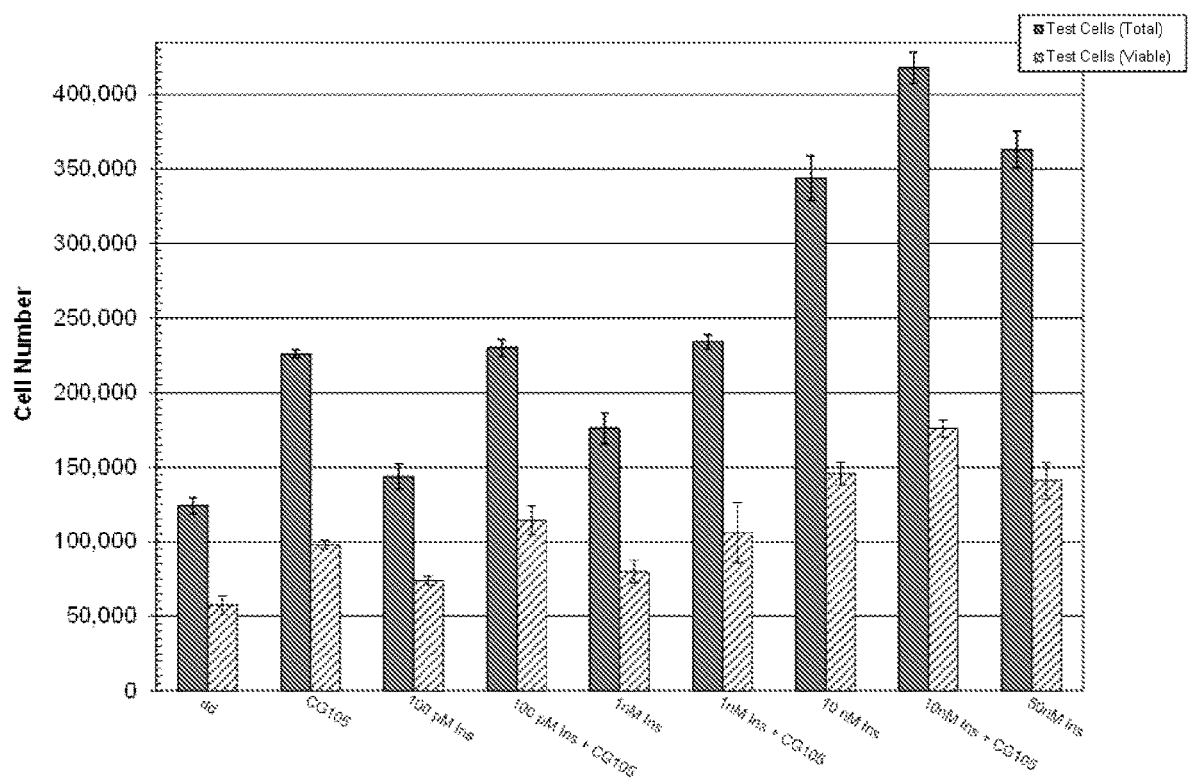

FIG. 5. shows selected extracts of the invention enhance the functioning of insulin in the IRS2 overproducing 32D Test cell system such that the amount of insulin necessary to achieve 100% stimulation of growth of the Test cells is lower than it would otherwise need to be in the absence of the selected extract. When CG-105 extract was added to low-dose insulin treatments on the 32D IRS2 Test Cell system, CG-105 extract was found to enhance the activity of insulin at all insulin doses below the maximum insulin stimulating effect (at 50 nM). This activity is variously referred to herein as Insulin Equivalent Activity (IEA) or Insulin Augmenting Activity (IAA), or the additional terms given herein.

DETAILED DESCRIPTION OF THE INVENTION

A substantial amount of effort has been made to attempt to identify plant extracts or compounds derived from plants that possess desirable effects for the treatment of human or animal disease. Numerous extracts, drinks, powders, teas, and so forth are marketed with claims relating to providing nutritional support for, or treatment of, many diseases, including diabetes and related metabolic disorders. None of these preparations has been demonstrated to activate the insulin mediated signal transduction cascade in an IRS2-specific manner (46-51, 53,54, 57-70,72, 74,75, 79-81). Zhang et al. conducted a high-throughput screen of more than 50,000 synthetic compounds and natural products and identified a compound that activated the Insulin Receptor (IR). The compound, however, turned out to not be derived from an edible plant source at all. Rather, the compound was derived from a fungal extract (Pseudomassaria) that had been recovered from leaves of an undetermined plant collected near Kinshasa, Democratic Republic of Congo. This work showed, however, that it was at least possible to identify a small molecule capable of having partial activity toward the Insulin Receptor (IR) (71). Prior to their work, it was believed that only a protein hormone such as insulin could activate its cognate receptor.

Pinent et al. demonstrated that a class of compounds known as procyanidins, which are derived from grape seeds, which can induce glucose lowering in an animal model, are able to bind to the IR and at least partially activate the receptor (60, 79). However, the authors concluded that the effects of the procyanidins result in activation of the insulin signaling cascade in a different manner than insulin does. Even with purified fractions of grape seed procyanodin extracts (GSPE), the authors were able to obtain only 40% of the activation of the IR as compared to insulin. In addition, the authors could not establish an IRS2-dependent effect of the compounds (79).

Thus, with the exception of insulin and its corresponding analogs and long-acting formulations, no compounds, including proteins, polypeptides or "small molecules" (i.e. molecules having a molecular weight of 2,000 atomic mass units or less) derived from a genus and species known to be edible have been shown to specifically activate the Insulin/Insulin Receptor/IRS2 signal transduction cascade in mammalian cells. In addition, no small molecules have been demonstrated to activate the insulin signaling cascade through an IRS-2 dependent manner. As discussed above in the Background of the Invention, such compounds, extracts, and methods of identifying them from any source would be desirable. This invention provides such compounds, and extracts derived from selected genera and species of edible plants containing this highly desirable activity.

The invention provides a method for the treatment, cure, prevention or nutritional support for various metabolic and other disorders including diabetes, pre-diabetes, metabolic syndrome, obesity, cancer, myelodysplastic syndromes, neurologic disorders such as Alzheimer's disease, dementia and cognitive impairment, attention deficit disorders, premature aging, cardiovascular disorders such as peripheral vascular disease, congestive heart failure, coronary artery disease and myocardial infarction, and others. The invention also provides compounds and extracts for the improvement of certain normal resting states such as baseline cognitive status, the cellular aging process, heart rate, stroke volume, blood pressure (systolic and diastolic), blood flow, cardiac output, and the basal metabolic rate of an organism. These beneficial aspects of the invention result, in part, by regulating the level or functional activity of IRS proteins as a result of administering an effective amount of the compounds or extracts of the invention to a subject in need or desiring thereof.

In one embodiment, the invention provides for restoring or enhancing insulin sensitivity in a cell by upregulating IRS2 function. The invention further provides a method of enhancing pancreatic β-cell function by upregulating IRS2 function. According to the invention, a disease or disorder characterized by reduced or insufficient signaling through IRS2 can be treated by upregulating IRS2 function. Such diseases include, but are not limited to, metabolic disease, diabetes, dyslipidemia, obesity, female infertility, central nervous system disorders, Alzheimer's disease, and disorders of angiogenesis.

According to the invention, upregulation of IRS2 function includes activation of IRS2 or a complex that includes IRS2. In one embodiment of the invention, upregulation of IRS2 function is also accomplished by activation of IRS2 activity, for example by inhibition of phosphorylation of specific serine, threonine or tyrosine residues of IRS2. In another embodiment, upregulation of IRS2 function is accomplished by enhanced expression of IRS2 or by inhibition of degradation of IRS2. In another embodiment, upregulation of IRS2 function is by modulation of a protein or nucleic acid molecule that participates in the mediation of an insulin effect on insulin-responsive cells. Also, modulation of the coupling function of the PH, PTB, or KRLB domains can improve IRS2 function.

More than one hundred samples of various edible plant genera and species were obtained from several local and international markets. Both aqueous and organic extractions of the fruits, leaves, stems and roots of various selected genera of edible plants and other plants were prepared. The extraction procedure was performed as follows: 500 milligrams of fresh plant tissue were pulverized with a mortar and pestle. The ground tissue was then added to 2 mL of water, and homogenized for 1 minute at a setting of 6 using a microprobe (Cole Palmer, LabGen 700). The mixture was then spun at 14,000 RPM for 10 minutes. The supernatant containing the aqueous layer was removed and assayed; whereas the pellet was retained and subjected to organic extraction procedure. Between procedures, samples were maintained at 4° C. to minimize endogenous enzymatic activities.

For larger scale extractions, the procedure was performed as follows: 250 g of wet plant tissue was added to 1 L of water, and initial tissue disruption was performed in a table top blender (Kitchen Aid). The blended mixture was then homogenized on ice for 5 minutes at a setting of 20 using a Polytron homogenizer and a standard size probe (Polytron PT2100). The mixture was spun at 10,000 RPM for 10 minutes at 4° C. using a JA-10 rotor (Beckman Coulter; Avanti J-251). The supernatant containing the aqueous layer was removed and assayed. Long term storage was either by refrigeration at 4° C. for up to three weeks, or portions of the sample were frozen and lyophilized.

It is preferable to maintain the pH of the extraction solution above 4.3. We have found that pH values of 4.3 and below may cause precipitation of the active factor from crude extracts, leading to a negative result in the 32D IRS2 cell-based assay system. If the solution is brought to pH values higher than 4.3, activity is restored. However, if the active factor is exposed to pH values that are lower (pH approximately 2.0 or less for extended periods), then restoration of activity by subsequently raising the pH is no longer possible, and the active factor becomes essentially irreversibly inhibited.

Under certain conditions, the active principle ("active factor", or simply "factor") obtained from CG-105 is susceptible to heat inactivation, whereas the factor is stable to freezing and lyophilization. Essentially no activity is extractable by the neat organic solvents tested, which included ethanol, methanol, phenol, chloroform, acetonitrile, and benzene.

In addition to emulating the effects of insulin on the Test cell line, it was observed that CG-105 and selected other extracts also increased the overall viability of the cells at the end of the assay on day 3, approximately 72 hours later (FIG. 5).

After the extraction procedure was complete, each extract obtained was assayed either directly using 1 microliter of aqueous extract derived from a 1 liter preparation using 250 grams of fresh plant material, as described above, or after redissolving 5 mg of lyophilized powder in 1 ml of distilled water and using 1 microliter per assay well in the 96 well format (approximately 100 microliter total media volume per well). The assay was performed on the 32D Test cell line stably overproducing IRS2 described above and previously (38). The Test cells consisted of 32D cells harboring a histidinol-selectable expression vector and containing a full-length gene encoding murine IRS2 under the transcriptional control of a promoter functional in 32D cells, whereas the Control cells consisted of 32D cells harboring the same histidinol-selectable expression vector lacking the IRS2 coding region.

Tables 1 and 2 show the results obtained with a variety of distinct genera and species of edible plants that Applicants' have discovered possess the desired activity. They are ranked according to their ability to stimulate growth of the IRS2-expressing Test cells as normalized to Insulin, with the response elicited by 50 nM Insulin treatment being defined as 100% (Table 1). The activities listed in Table 1 are among the highest that were obtained from numerous experiments. Considerable variations in activity from lot to lot of plant material may be expected depending upon the time of year that the plant was grown and harvested, the degree of freshness of the plant, the soil and climate conditions in which it was propagated, and so on.

Tables 1 and 2 shows the activities of several of the most active aqueous extracts obtained from selected species. Activities are reported as a percentage of the total insulin activity obtained using 50 nM Insulin as the positive control for signaling through the IRS2 branch of the signal transduction cascade. Table 2 shows the increase in growth of the Test cells relative to the Control cells for each extract that was tested. (The values indicated are determined by subtracting the mean values of the Control cells from the Test cells for each extract, respectively, as shown in Table 1. (Mean and standard deviations for each extract value are as given in Table 1). As is evident from results shown in Table 2, which are organized taxonomically, certain aqueous extracts exhibit insulin like biological activity in the 32D IRS2 Test cell system equal to as much as 40% of the response obtained with insulin. Positively scoring activities ranged from a low of 10% to a high of 40% of the amount of the cellular response obtained with insulin. One of the families shown in Table 2, the Asteraceae family, contains genera and species which uniformly scored positively, though to varying degrees. Other families, such as Lamiaceae or Brassicaceae, contained some members which scored positively and others which were negative. Finally, all of the members of the Amaranthaceae family that were tested were essentially negative (ND=no activity detected).

TABLE 1

Natural Product Activity Relative to Insulin

| NP | Control Cells ($32D^{his}$) | Test Cells ($32D^{IRS2}$) |
|---|---|---|
| | X ≤ 10% | |
| CG148 | −0.1 ± 1.1 | 3.9 ± 1.3 |
| CG158 | 0.1 ± 2.0 | 3.9 ± 1.3 |
| CG137 | −0.1 ± 2.9 | 6.1 ± 1.2 |
| CG126 | 1.6 ± 0.8 | 6.9 ± 1.4 |
| CG144 | −1.7 ± 0.9 | 7.3 ± 2.4 |
| CG118 | 0.6 ± 0.1 | 7.8 ± 0 |
| CG149 | 2.1 ± 1.3 | 7.8 ± 0 |
| CG128 | 2.0 ± 3.0 | 8.3 ± 5.6 |
| CG141 | 0.2 ± 0.2 | 8.5 ± 1.2 |
| CG146 | 1.1 ± 1.3 | 8.5 ± 1.2 |
| CG154 | 2.5 ± 1.3 | 9.1 ± 3.9 |
| CG156 | 2.5 ± 0 | 9.1 ± 1.3 |
| CG142 | 1.0 ± 2.9 | 9.8 ± 0 |
| | 10% < X ≤ 20% | |
| CG153 | 2.8 ± 2.4 | 10.4 ± 2.6 |
| CG104 | 3.2 ± 0.4 | 10.5 ± 2.6 |
| CG113 | 4.3 ± 1.9 | 10.5 ± 2.6 |
| CG123 | 4.6 ± 1.8 | 11.8 ± 3.9 |
| CG136 | 0.7 ± 0.4 | 12.2 ± 0 |
| CG131 | 1.2 ± 2.4 | 13.9 ± 0 |
| CG159 | 0.8 ± 0.4 | 14.3 ± 1.3 |
| CG115 | 0 ± 0.7 | 15.7 ± 0 |
| CG121 | 2.5 ± 1.8 | 15.7 ± 7.8 |
| CG107 | 4.3 ± 0.8 | 15.8 ± 7.9 |
| CG112 | 0.4 ± 1.3 | 15.8 ± 2.6 |
| CG125 | 1.3 ± 1.8 | 16.7 ± 5.6 |
| CG155 | 1.3 ± 2.5 | 16.9 ± 1.3 |
| CG114 | 0.4 ± 1.5 | 17.6 ± 9.8 |
| CG139 | −1.0 ± 1.2 | 18.3 ± 1.2 |
| CG140 | 0.7 ± 1.1 | 19.5 ± 2.4 |
| CG157 | 2.0 ± 2.1 | 19.5 ± 3.9 |
| | 20% < X ≤ 25% | |
| CG138 | 0.1 ± 1.6 | 20.7 ± 1.2 |
| | X > 25% | |
| CG120 | −0.3 ± 0.1 | 25.5 ± 2.0 |
| CG143 | −2.5 ± 0.3 | 25.6 ± 3.7 |
| CG132 | −0.6 ± 1.1 | 26.4 ± 1.4 |
| CG135 | 0 ± 0 | 26.8 ± 4.9 |
| CG110 | 1.9 ± 2.1 | 31.6 ± 7.9 |
| CG150 | 2.4 ± 1.0 | 33.8 ± 5.2 |
| CG105 | 0.6 ± 0 | 36.8 ± 7.9 |

TABLE 2

Natural Product Activity Relative to Insulin

| NP | Genus_species | % Activity above baseline ($T_A - C_A$) |
|---|---|---|
| | Taxonomic Family: Amaranthaceae | |
| CG101 | *Beta vulgaris* | ND |
| CG102 | *Beta vulgaris* | ND |
| CG103 | *Beta vulgaris* | ND |
| CG111 | *Spinacia oleracea* | ND |
| CG116 | *Beta vulgaris* | ND |
| CG117 | *Beta vulgaris* | ND |
| | Taxonomic Family: Apiaceae | |
| CG127 | *Petroselium hortense* | ND |
| CG133 | *Apium graveolens* | ND |
| CG134 | *Apium graveolens* var. *dulce* | ND |
| CG126 | *Petroselinum crispum* | 5 |
| CG128 | *Coriandrum sativum* | 6 |
| CG118 | *Petroselinum crispum* | 7 |
| CG146 | *Anethum graveolens* | 7 |
| CG107 | *Daucus carota* | 12 |
| CG112 | *Petroselinum crispum* | 15 |
| | Taxonomic Family: Asteraceae | |
| CG104 | *Cichorium endivia* | 7 |
| CG123 | *Taraxacum officinale* | 7 |
| CG131 | *Cichorium endivia* | 13 |
| CG125 | *Lactuca sativa* | 15 |
| CG114 | *Lactuca sativa* | 17 |
| CG120 | *Lactuca sativa* var. *crispa* (rd leaf) | 26 |
| CG143 | *Cynara scolymus; Cynara cardunculus* | 26 |
| CG132 | *Lactuca sativa* var. *crispa* (gr. leaf) | 26 |
| CG135 | *Artemisia dracunculus* | 27 |
| CG110 | *Lactuca sativa* var. *longifolia* | 30 |
| CG105 | *Cichorium endivia* var. *latifolium* | 36 |
| | Taxonomic Family: Brassicaceae | |
| CG109 | *Brassica oleracea* var. *italica* | ND |
| CG119 | *Brassica oleracea* var. *viridis* | ND |
| CG124 | *Brassica oleracea* var. *capitata* | ND |
| CG129 | *Brassica oleracea* var. *viridis* | ND |
| CG145 | *Brassica oleracea* var. *gemmifera* | ND |
| CG156 | *Nasturtium officinalis* | 7 |
| CG153 | *Brassica rapa* | 8 |
| CG142 | *Eruca sativa* | 9 |
| CG136 | *Brassica rapa* | 12 |
| CG121 | *Brassica nigra* | 13 |
| CG115 | *Brassica rapa chinensis* | 16 |
| | Taxonomic Family: Cucurbitaceae | |
| CG152 | *Cucurbita pepo* var. *pepo* | ND |
| CG141 | *Cucumis sativus* | 8 |
| | Taxonomic Family: Fabaceae | |
| CG150 | *Phaseolus vulgaris* | 31 |
| | Taxonomic Family: Lamiaceae | |
| CG122 | *Mentha piperita* | ND |
| CG137 | *Origanum vulgare* | 6 |
| CG154 | *Rosmarinus officinalis* | 7 |
| CG159 | *Ocimum basilicum* | 14 |
| CG155 | *Salvia officinalis* | 16 |
| CG140 | *Origanum majorana* | 19 |
| CG138 | *Thymus vulgaris* | 21 |
| | Taxonomic Family: Liliaceae | |
| CG106 | *Allium cepa* | ND |
| CG130 | *Asparagus officinalis* | ND |
| CG113 | *Allium porrum* | 6 |
| CG139 | *Allium schoenoprasum* | 18 |
| | Taxonomic Family: Poaceae | |
| CG158 | *Cymbopogon* | 4 |
| CG157 | *Agropyron Gaertn* | 18 |

TABLE 2-continued

Natural Product Activity Relative to Insulin

| NP | Genus_species | % Activity above baseline ($T_A - C_A$) |
|---|---|---|
| | Taxonomic Family: Polygonaceae | |
| CG148 | Rheum ribes | 4 |
| | Taxonomic Family: Solanaceae | |
| CG151 | Solanum lycopersicum | ND |
| CG149 | Solanum melongena | 6 |
| CG144 | Capsicum L. | 7 |
| | Taxonomic Family: Vitaceae | |
| CG147 | Vitis vinifera; Vitis L. | ND |

Based upon the direct comparison to insulin's ability to activate the IRS2 overproducing Test cells, Applicants define the measurement of such activity in the following ways:
  Insulin Sensitizing Units—(IS units)
  Insulin Sensitizing Activity (ISA units)
  Insulin Optimizing Activity—(IOA units)
  Insulin Optimizing Units—(1O units)
  Insulin Boosting Activity—(IBA units)
  Insulin Boosting Units—(IB units)
  Insulin Amplifying Units—(IA units)
  Insulin Amplifying Activity—(IAA units)
  Insulin Intensifying Units—(IIn units)
  Insulin Intensifying Activity—(IInA units)
  Insulin Augmenting Activity—(IAA units)
  Insulin Improving Activity—(IImA units)
  Insulin Improving Units—(IIm units)
  Insulin Strengthening Units—(ISt units)
  Insulin Enriching Units—(IEn units)
  Insulin Equivalent Units—(IEq units)
  Insulin Equivalent Activity—(IEA units)

One Unit of Insulin Equivalent Activity (also known as Insulin Augmenting Activity) is defined as the minimum amount of material (compound or extract) necessary to increase the growth of the IRS2 overproducing TEST cells by 1% of the level of growth achieved by treatment of the cells with an appropriate amount of insulin necessary to achieve a substantial increase in growth of the Test cells that a skilled investigator would classify as a sufficient positive control result. This is measured in terms of percentage relative to the maximum effect achieved with Insulin treatment under said positive control conditions. For these purposes, and as shown in the experiments of Tables 1 & 2 and FIG. 5, 50 nM insulin is utilized as the positive control. This amount has been determined empirically based upon each lot of insulin that is purchased. By way of example, if 1 microliter of plant extract increases the growth of the IRS2 Overproducing 32D Cell line by 20% in the 96-well plate format assay described above, relative to a positive control comprising 50 nM Insulin treatment (normalized to 100%), then said extract is considered to contain 20 units of Insulin Equivalent (or Insulin Augmenting) Activity. In our experience, 50 to 100 nM Insulin is a saturating amount of insulin under most conditions.

Using standard methodologies for extraction, purification, and filtration, including size-exclusion chromatography, normal and reversed-phase high-pressure liquid chromatography (HPLC), hydrophilic interaction chromatography (HILIC), affinity chromatography, non-sterile and sterile filtration methods, and the like, such activities may be concentrated and increased to as much as 100% of the effect of insulin on the IRS2 Overproducing 32D Cell line (82-84, and references therein). Thus, in one embodiment, the invention provides a botanical extract that contains at least $1\times10^3$ Insulin Equivalent (IE) units per milliliter. In another embodiment, the invention provides a botanical extract that contains at least $1\times10^4$ IE units per milliliter. In another embodiment, the invention provides a botanical extract that contains at least $2\times10^4$ IE units per milliliter. In still another embodiment, the invention provides a botanical extract that contains at least $3.6\times10^4$ IE units per milliliter. In another embodiment, the invention provides a botanical extract that contains from $1\times10^3$ to $1\times10^4$ IE units per milliliter. In yet another embodiment, the invention provides a botanical extract that contains from $1\times10^4$ to $1\times10^5$ IE units per milliliter. In yet another embodiment, the invention provides a botanical extract that contains from $1\times10^5$ to $1\times10^6$ IE units per milliliter. In still another embodiment, the invention provides a botanical extract that contains from $1\times10^6$ to greater than $1\times10^7$ IE units per milliliter.

Extraction methods include the use of aqueous-based solvents in neutral, basic or weakly acidic pH ranges, or $CO_2$-mediated extraction. Purification methods include size-exclusion chromatography using pore-containing silica-based or polymeric beads for separations depending upon the relative molecular size of a bioactive molecule. Additional purification methods may utilize hydrophobic column matrices (C4 or C18-substituted beads), various hydrophilic interaction chromatography (HILIC) media such as hydroxyl, di-hydroxyl, amide, amino, cyano, and related substituted side chains, affinity chromatography media, or ion exchange media employing amino or carboxylic acid moieties cross-linked to a 3 or 5 micron beads. Sterile or non-sterile filtration methods include filter papers such as Whatman 3MM, sterile nylon-membrane-based filters with 0.45 or 0.2 micron exclusion cutoffs, insoluble filtration medias such as glass wool, cellulose, silica, diatomaceous earth (DE), nylon fabric, stainless steel plates containing micron and submicron sized pores, crossflow cartridge filtration systems, centrifugation-based separation, and the like.

Disclosed herein is a botanical extract that provides at least $1\times10^4$ to $1\times10^5$ Insulin Equivalent units in 1 milliliter where the botanical extract comprises extracts from *Artemisia dracunculus, Cichoria endivia* and *Lactuca sativa* and a metal (e.g., chromium, iron, manganese, zinc, or copper). In certain embodiments, the extracts from *Artemisia dracunculus, Cichoria endivia* and *Lactuca sativa* are dried aqueous extracts where the aqueous extracts are produced by a process comprising extracting leaves of *Artemisia dracunculus, Cichoria endivia* and *Lactuca sativa*.

Also disclosed herein is a pharmaceutical composition or nutritional supplement comprising the extracts described above, optionally in combination with a metal. The pharmaceutical composition or nutritional supplement may be in a conventional dosage form, e.g., a tablet or a capsule such as a hard- or soft-shelled gelatin or hydroxypropylmethylcellulose capsule. The pharmaceutical composition or nutritional supplement may also be in the form of a powder, e.g., a maltodextrin-containing powder, which may be reconstituted into solution by dissolving in water or another suitable liquid before use.

In one embodiment, the pharmaceutical composition or nutritional supplement in tablet or capsule form comprises:
  a dried herbal extract of *Artemisia dracunculus*;
  a dried herbal extract of *Cichoria endivia*;
  a dried herbal extract of *Lactuca sativa*; and
  optionally, chromium.

In certain embodiments, the pharmaceutical composition or nutritional supplement is in tablet form. In certain embodiments, the pharmaceutical composition or nutritional supplement in tablet form comprises:

0.7 mg of a dried herbal extract of *Artemisia dracunculus*;
962.7 mg of a dried herbal extract of *Cichoria endivia*;
16.7 mg of a dried herbal extract of *Lactuca sativa*; and
1.2 mcg chromium;
optionally also comprising at least one pharmaceutically acceptable excipient selected from the group consisting of: dicalcium phosphate, microcrystalline cellulose, silicon dioxide, hydroxypropyl cellulose, stearic acid, croscarmellose sodium, and magnesium stearate; and combinations thereof.

In certain embodiments, the pharmaceutical composition or nutritional supplement is in tablet, capsule, or powder form. In certain embodiments, the pharmaceutical composition or nutritional supplement in tablet, capsule, or powder form comprises:

a total of 50 mg to 1,500 mg of:
a dried herbal extract of *Artemisia dracunculus*;
a dried herbal extract of *Cichoria endivia*;
a dried herbal extract of *Lactuca sativa*; and
optionally, chromium.
optionally also comprising at least one pharmaceutically acceptable excipient selected from the group consisting of: dicalcium phosphate, microcrystalline cellulose, silicon dioxide, hydroxypropyl cellulose, stearic acid, croscarmellose sodium, and magnesium stearate; and combinations thereof.

In certain embodiments, the at least one pharmaceutically acceptable excipient is present in an amount of 15-25% of the total weight. In certain embodiments, the extracts of *Artemisia dracunculus*, *Cichoria endivia* and *Lactuca sativa* are present in a ratio of about 1:1,375:24 (w/w/w).

Disclosed herein is method of treating an IRS mediated disease or condition comprising administering an effective amount of the pharmaceutical compositions or nutritional supplements described above to a subject in need thereof. In certain embodiments, the IRS mediated disease or condition is diabetes, pre-diabetes, metabolic syndrome, insulin resistance, or dementia. In certain embodiments, the method further comprises administering an antidiabetic agent, insulin, metformin, exenatide, vildagliptin, sitagliptin, a DPP4 inhibitor, meglitinide, exendin-4, liraglutide, or a GLP1 agonist. The pharmaceutical composition or nutritional supplement disclosed above may be administered in a separate pharmaceutical formulation from the antidiabetic agent, insulin, metformin, exenatide, vildagliptin, sitagliptin, a DPP4 inhibitor, meglitinide, exendin-4, liraglutide, or GLP1 agonist. Alternatively, the pharmaceutical composition or nutritional supplement disclosed above may be administered in the same pharmaceutical formulation as the antidiabetic agent, insulin, metformin, exenatide, vildagliptin, sitagliptin, a DPP4 inhibitor, meglitinide, exendin-4, liraglutide, a sodium-glucose transporter type 2 (SGLT-2) inhibitor such as empagliflozin, canagliflozin, or dapagliflozin, or a GLP1 agonist. In certain embodiments, the pharmaceutical composition or nutritional supplement is administered orally twice per day, 30-60 minutes before meals.

Disclosed herein is a method of stimulating IRS2-dependent signal transduction in a subject in need thereof comprising administering to the subject an effective amount of the pharmaceutical compositions or nutritional supplements described above.

Disclosed herein is a method of stimulating IRS2-dependent signal transduction comprising contacting a cell with the pharmaceutical compositions or nutritional supplements described above.

This invention provides compounds and methods of providing nutritional support, preventing, inducing durable long-term remissions or curing patients with diabetes, metabolic disorders, central nervous system diseases, obesity, fertility and other human disorders as discussed above. The invention is particularly concerned with the IRS proteins and with modulation of the activity of IRS2-mediated cellular signaling pathways as a mechanism for treating human disease and/or providing beneficial nutritional support.

The invention also provides an assay to select for specific cultivars with even higher activity or selecting progeny from crosses of cultivars or species for selecting individuals again with high levels of activity. The invention also provides for the use of combinations of two or more individually active species, including variants.

One feature of the present invention provides IRS branch activators. The invention provides a method of modulating an Insulin Receptor Substrate (IRS) function comprising contacting the IRS (including a cell or tissue comprising the IRS) with a compound, plant fragment, extract of said plant fragment, or an extract derived from the genus and species of plant that has been shown to provide a positive result in the IRS2 specific cell-based assay system described above. Such plants include, but are not limited to, those disclosed in Tables 1 and 2. One possessing a high degree of skill in this field is well aware that genera of plants may evolve independently of one another and yet produce metabolites that are chemically similar or even identical in structure. As an example glucosinolates as a compound class includes more than 100 compounds that are produced by many plants of the Brassicales order which includes more than 4,000 species including mustard, cabbage, broccoli, papaya. A single glucosinolate, such as sulforaphane, is found in high quantities in broccoli but is also present in brussel sprouts, cauliflower, turnip, watercress, bok choy and many other cruciferous vegetables (85). Another example is the production of latex by plants, which occurs in approximately 10% of all plant species, some 40 families including multiple lineages of the two major groups of angiosperms (flowering plants, division Magnoliophyta) the dicots (broad leaf) and monocots (grasses), as well conifers (pine trees, division Pinophyta) and pteridophytes (mosses, ferns, division Pteridophyta). These two examples of compounds being produced by different species, families and genera (for glucosinolates) or further across evolution to different orders, classes and phyla for latex indicate that similar or identical compounds can be produced by unrelated plants across evolution (77,78). Therefore, no limitation is intended on the type of plant extract or purified compound that is capable of providing insulin augmenting activity, wherein such activity may be identified through the use of the IRS2 overproducing Test cells described herein and elsewhere (20, 38). The change in a cellular phenotype (including cell proliferation), activity of the IRS, expression of the IRS, phosphorylation of IRS, or other downstream targets in the IRS2 signal transduction cascade, or binding of the IRS to another insulin receptor or insulin-like growth factor receptor signal transduction pathway component may be monitored. IRS modulation with a compound of the invention may be in treatment or prevention of a4 disease, or in biological assays, cellular assays, biochemical assays, or the like.

Compounds of the invention may be identified using 32D cells expressing a selected IRS family member. Such cells may be created using standard methodology originally invented by one of the Applicants and previously described in detail (38). Briefly, 32D cells expressing a selected IRS family member (Test cells) and 32D Cells that essentially do not express the selected IRS family member (Control cells) are brought into contact with a test compound. Compounds of the present invention will have a more pronounced effect on the Test cells than on the Control cells.

The present invention also provides methods of preventing, treating, or ameliorating an IRS mediated disease or condition comprising identifying a patient in need, and administering a therapeutically or nutraceutically effective amount of a compound or an extract alone or together with a pharmaceutically acceptable salt, ester, amide, or prodrug thereof. IRS mediated diseases or conditions include, without limitation, diabetes (type 1 and type 2), insulin resistance, metabolic syndrome, dementia, Alzheimer's disease, hyperinsulinemia, dyslipidemia, and hypercholesterolemia, obesity, hypertension, retinal degeneration, retinal detachment, Parkinson's disease, cardiovascular diseases including vascular disease, atherosclerosis, coronary heart disease, cerebrovascular disease, heart failure and peripheral vascular disease in a subject.

As shown in FIGS. 2 and 3, a 75g raw dose of a selected genus and species (*Cichorium endivia*, var. latifolium; designated CG-105), when administered orally, lowers fasting blood glucose in a human being. The volunteer test subjects are the Applicants. Arrows indicate time of oral administration. Also shown in FIG. 2 are analogous human results of fasting blood glucose before and after administration of a 1.9 gram dose of lyophilized aqueous extract prepared from CG-105 and administered in gelatin capsules. These results demonstrate that this species of plant is capable of inducing a modest fasting blood glucose lowering effect in non-diabetic human beings.

Modulation of IRS function can involve one of the following non-limiting mechanisms. One possible mechanism involves modifying (i.e., promoting or inhibiting) the IRS2 binding interaction with various proteins both upstream and downstream that interact with (bind to) IRS2. These include, for example, the human Insulin Receptor (hIR) which binds to and phosphorylates IRS1 and IRS2, the N-terminal c-jun kinase (JNK), PKC isoforms, ERK1 or ERK2, as well additional upstream or downstream signaling elements such as src homology 2 (SH2) domain-containing proteins that bind to IRS2 and may also phosphorylate, dephosphorylate or otherwise modify IRS.

Another mechanism involves changing the specific pattern of covalent modifications of IRS such as the phosphorylation state of serine, threonine and tyrosine residues, ubiquitination patterns, acetylation or other covalent modifications that alter the function, intracellular localization, or stability of IRS proteins.

A third mechanism involves controlling the expression of the IRS genes in specific cells, including beta cells, brain cells, liver cells muscle cells, reproductive cells and tissues involved in reproduction, fat cells, mammary cells, bone cells and immune system cells, essentially any cells of the body where IRS2 might be naturally expressed. IRS2 is regulated by transcription factors such as CREB, CRTC2, Foxo1, TFE3, and SREBP1. Accordingly, increased IRS2 expression can result from increased activity of the transcription factors that stimulate the transcription of the IRS2 genes. IRS2 expression is also modulated in part by cAMP levels.

IRS is sensitive to proteolytic degradation. Accordingly, compounds that interfere with IRS degradation, for example by interacting with IRS to block degradation or by inhibiting a protease directly, can be used to upregulate IRS signaling activity.

Methods for assessing the effects of compounds of the invention on IRS signaling, in vitro and in vivo, are known in the art. For example, cell based assays can be used to confirm increases in IRS signaling. Further, various experimental strategies are available to confirm IRS function, including measuring glucose uptake in response to insulin stimulation, or determining expression of known downstream genes. To observe regulation of IRS expression, reporter genes linked to IRS expression control sequences may be constructed.

Compounds of the invention that upregulate the expression or cellular activity of IRS are used to promote IRS signaling. Upregulating IRS in specific tissues can target or prevent diseases involving those specific tissues or cells. For example, upregulation of IRS2 in pancreatic β-cells improves glucose stimulated insulin secretion. Drugs that upregulate the IRS2 gene or promote IRS2 signaling in β-cells will promote β-cell function and are useful to treat or prevent diabetes. Further, the level or functional activity of IRS2 can be modulated in human beings and other mammals in order to ameliorate or prevent the failure or destruction of pancreatic β-cells that causes certain forms of diabetes, and reduce the need for insulin by peripheral insulin sensitive tissues.

IRS genes also functions in peripheral tissues that respond to insulin. Upregulation of the IRS2 gene or upregulation of IRS2 signaling function makes tissues more sensitive to insulin and thus less insulin is needed to elicit an appropriate response. In one embodiment, a single compound of the invention promotes IRS2 gene expression or IRS2 function in multiple tissues, for example, promoting insulin secretion in β-cells and insulin sensitivity in other cells and tissues, including, but not limited to, hepatocytes and neurons. In another embodiment, two or more compounds of the invention are used to promote IRS activity in different cells or tissues. In some instances, two or more such compounds may be contained within an extract derived from a single species of plant. These effects of IRS work together to keep glucose under control and prevent diabetes and related disorders that are modulated by IRS function.

Upregulation of IRS expression or an increase of IRS signaling function is also useful to treat other diseases and disorders. Compounds that promote IRS function are useful for reversing catabolism during acute trauma. Insulin resistance is a major problem during acute trauma. Decreased insulin secretion during acute trauma exacerbates autophagy, which increases muscle and tissue wasting that can progress to kidney disease. Insulin resistance and decreased insulin secretion leads to massive catabolism that can threaten survival in the early period of repair. Both processes can be explained in part by the loss of IRS signaling due to inhibition by inflammatory processes and activation of autophagy. Drugs that promote IRS2 function, prevent IRS2 degradation, or promote IRS2 expression reverse these effects.

A major problem with obesity is that peripheral tissues become insulin resistant; if β-cells fail to make enough insulin to overcome the insulin resistance then diabetes develops. Applicants have previously discussed how insulin resistance and diabetes can be treated with compounds that upregulate IRS2 in β-cells and/or peripheral tissues. Upregulating IRS2 in β-cells promotes glucose sensitivity and insulin secretion, and upregulating IRS2 in peripheral tissues reduces the insulin requirements. Accordingly, the incidence of life threatening complications of obesity can be reduced.

Approximately half of the growth of a mouse brain depends on the expression of the IRS2 gene. Drugs that promote IRS2 signaling promote neural growth and regeneration in mammals and people. IRS2 signaling also plays a role in dephosphorylation of the Tau protein, a marker of Alzheimer disease. Upregulation of IRS2 in the hippocampus should promote normal function and contribute to the prevention of the neuronal degeneration associated with Alzheimer disease. Accordingly, compounds and extracts of the invention will be beneficial for dementia, including Alzheimer's disease.

IRS2 signaling also plays a role in feeding behavior. Mice lacking IRS2 tend to gain weight as a result of the inability of the brain to properly assess whether insulin has been secreted or not after a meal, so the brain can not determine whether a meal has in fact been consumed. Upregulation of IRS2 in the hypothalamus, and particularly the arcuate nucleus of the hypothalmus, will promote appetite regulation that results in reduced weight gain or even weight loss IRS2 signaling plays a role in fertility. Notably, female mice lacking IRS2 are infertile. By upregulating IRS2 signaling or IRS2 gene expression in pituitary gonadotrophs or ovaries, ovulation may be enhanced IRS2 promotes retinal growth. Mice lacking IRS2 display increased loss of retinal neurons, especially rod and cones, leading to blindness. Thus, compounds of the invention are useful for reducing or preventing retinal degeneration and promoting retinal growth and regeneration.

The invention also provides for coadministration of a compound or extract alone or together with a pharmaceutically acceptable salt, ester, amide, prodrug, or solvate, to a subject in combination with a second therapeutic agent or other treatment.

Second therapeutic agents for treatment of diabetes and related conditions include biguanides (including, but not limited to metformin), which reduce hepatic glucose output and increase uptake of glucose by the periphery, insulin secretagogues (including but not limited to sulfonylureas and meglitinides, such as repaglinide) which trigger or enhance insulin release by pancreatic β-cells, and PPARγ, PPARα, and PPARα/γ modulators (e.g., thiazolidinediones such as pioglitazone and rosiglitazone).

Additional second therapeutic agents include GLP1 receptor agonists, including but not limited to GLP1 analogs such as exendin-4 and liraglutide and agents that inhibit degradation of GLP1 by dipeptidyl peptidase-4 (DPP-4). Vildagliptin and sitagliptin are non-limiting examples of DPP-4 inhibitors.

Still other second therapeutic agents include the sodium glucose transporter type 2 (SGLT-2) inhibitors, which reduce the ability of the kidney to reabsorb glucose after it passes through the glomerulus and into the nephron. SLGT-2 inhibitors including, but not limited to empagliflozin, canagliflozin, or dapagliflozin inhibit reabsorption of glucose by the nephron resulting in large amounts of glucose remaining in the urine. This class of compounds has a significant blood glucose lowering effect but also markedly increases the likelihood of bladder infections and pyelonephritis due to the resulting glucosuria.

In certain embodiments of the invention, compounds or extracts are coadministered with insulin replacement therapy.

According to the invention, compounds or extracts are coadministered with statins and/or other lipid lowering drugs such as MTP inhibitors and LDLR upregulators, antihypertensive agents such as angiotensin antagonists, e.g., losartan, irbesartan, olmesartan, candesartan, and telmisartan, calcium channel antagonists, e.g. lacidipine, ACE inhibitors, e.g., enalapril, and β-andrenergic blockers (β-blockers), e.g., atenolol, labetalol, and nebivolol.

In another embodiment, a subject is prescribed a compound or extract of the invention in combination with instructions to consume foods with a low glycemic index.

In a combination therapy, the compound or extract is administered before, during, or after another therapy as well as any combination thereof, i.e., before and during, before and after, during and after, or before, during and after administering the second therapeutic agent. For example, a compound or extract of the invention can be administered daily while extended release metformin is administered daily (55, 56). In another example, a compound of the invention is administered once daily and while exenatide is administered once weekly. Also, therapy with a compound or extract of the invention can be commenced before, during, or after commencing therapy with another agent. For example, therapy with a compound or extract of the invention can be introduced into a patient already receiving therapy with an insulin secretagogue. In addition, compounds or extracts of the present invention may be administered once or twice daily in conjuction with other nutritional supplements, vitamins, nutraceuticals, or dietary supplements. Examples include GCE, chlorogenic acid, chicoric acid, cinnamon and various other hydroxycinnamic acids, chromium, chromium picolinate, a multivitamin, and so on.

In another aspect, the present invention provides pharmaceutically acceptable compositions which comprise a therapeutically-effective amount of one or more of the compounds or extracts of the present invention, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

In another aspect, the present invention provides nutritionally beneficial or supportive compositions which comprise a nutritionally beneficial or supportive amount of one or more of the compounds or extracts of the present invention, formulated together with one or more active or inactive ingredients carriers (additives) and/or diluents. As described in detail below, the nutritional supplement formulations of the present invention may be specially formulated for administration in solid or liquid form, including those adapted for the following: (1) oral administration, for example, drinks, foods, chewable pastes or gums, drenches (aqueous or non-aqueous solutions or suspensions), capsules, tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment, e.g. reasonable side effects applicable to any medical treatment.

The phrase "nutritionally-effective amount" as used herein means that amount of a compound, material, composition comprising an extract of the present invention which is effective for producing some desired nutritional effect in at least a sub-population of cells in an animal at a reasonable benefit/risk ratio applicable to any nutritional supplement, e.g. reasonable side effects applicable to any nutritional supplement.

The term "composition" whether in singular or plural form, refers both to discrete, chemically defined molecules as well as extracts from plants and other biological organisms containing active ingredients that show a positive result in the IRS2 Cell-based assay system described above.

The phrase "pharmaceutical composition" necessarily includes, when appropriate, nutraceutical compositions, nutritional/dietary supplements, and the like.

The phrase "pharmaceutically acceptable" is employed herein to refer to those compounds, materials, compositions, and/or dosage forms which are, within the scope of sound medical judgment, suitable for use in contact with the tissues of human beings and animals with toxicity, irritation, allergic response, or other problems or complications, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose, cellulose acetate, and hydroxyl propyl methyl cellulose; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

By the term "metal" is meant any element of the periodic table, including but not limited to those elements also known as "transition metals", "inner-transition metals", and "post-transition metals" that is generally considered to have metallic chemical properties and is capable of being present within the body of a mammal without resulting in toxicity or death of the mammal. Examples of a metals embraced by this definition include, but are not limited to, lithium, beryllium, sodium, magnesium, aluminum, potassium, calcium, scandium, titanium, vanadium, chromium, manganese, iron, cobalt, nickel, copper, zinc, gallium, and the like. (86)

As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like (37).

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example. 37).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient may be mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical and nutraceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, nutraceuticals, or nutritional supplements to humans and animals, they can be given per se or as a composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical or nutritional composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic or nutritionally supportive effect. Such an effective dose will generally depend upon the factors described above. Generally, oral, intravenous, intracerebroventricular and subcutaneous doses of the compounds of this invention for a patient, when used for the indicated analgesic effects, will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms. Preferred dosing is one administration per day.

While it is possible for a compound of the present invention to be administered alone, it is preferable to administer the compound as a pharmaceutical formulation or a nutritional formulation, both of which are termed "compositions" herein.

The compounds according to the invention may be formulated for administration in any convenient way for use in human or veterinary medicine, by analogy with other pharmaceuticals, nutraceuticals, or nutritional supplements.

REFERENCES

1. White M F. Insulin signaling in health and disease. Science 2003 Dec. 5; 302 (5651):1710-1.
2. Nakayama M, Abiru N, Moriyama H, Babaya N, Liu E, Miao D, et al. Prime role for an insulin epitope in the development of type 1 diabetes in NOD mice. Nature 2005 May 12; 435 (7039):220-3.
3. Meier J J, Bhushan A, Butler A E, Rizza R A, Butler P C. Sustained beta cell apoptosis in patients with long-standing type 1 diabetes: indirect evidence for islet regeneration? Diabetologia 2005 November; 48 (11):2221-8.
4. Semple R K, Sleigh A, Murgatroyd P R, Adams C A, Bluck L, Jackson S, et al. Postreceptor insulin resistance contributes to human dyslipidemia and hepatic steatosis. J Clin Invest 2009 February; 119 (2):315-22.
5. Vaxillaire M, Veslot J, Dina C, Proenca C, Cauchi S, Charpentier G, et al. Impact of common type 2 diabetes risk polymorphisms in the DESIR prospective study. Diabetes 2008 January; 57 (1):244-54.
6. DeFronzo R A. Pathogenesis of type 2 diabetes mellitus. Med Clin North Am 2004 July; 88 4):787-835, ix.
7. Brownlee M. The pathobiology of diabetic complications: a unifying mechanism. Diabetes 2005 June; 54 (6):1615-25.
8. Barbieri M, Rizzo M R, Manzella D, Grella R, Ragno E, Carbonella M, et al. Glucose regulation and oxidative stress in healthy centenarians. Exp Gerontol 2003 January; 38 (1-2):137-43.
9. Clemmons D R. Involvement of insulin-like growth factor-I in the control of glucose homeostasis. Curr Opin Pharmacol 2006 December; 6 (6):620-5.
10. White M F, Kahn C R. The insulin signaling system. J Biol Chem 1994; 269 (1):1-4.
11. White M F, Shoelson S E, Keutmann H, Kahn C R. A cascade of tyrosine autophosphorylation in the beta-subunit activates the phosphotransferase of the insulin receptor. J Biol Chem 1988 Feb. 25; 263 (6):2969-80.
12. Till J H, Ablooglu A J, Frankel M, Bishop S M, Kohanski R A, Hubbard S R. Crystallographic and solution studies of an activation loop mutant of the insulin receptor tyrosine kinase: insights into kinase mechanism. J Biol Chem 2001 Mar. 30; 276 (13):10049-55.
13. Hubbard S R. Crystal structure of the activated insulin receptor tyrosine kinase in complex with peptide substrate and ATP analog. EMBO J 1997; 16 (18):5572-81.
14. White M F, Livingston J N, Backer J M, Lauris V, Dull T J, Ullrich A, et al. Mutation of the insulin receptor at tyrosine 960 inhibits signal transmission but does not affect its tyrosine kinase activity. Cell 1988; 54:641-9.
15. Yenush L, White M F. The IRS-signaling system during insulin and cytokine action. Bio Essays 1997; 19(5): 491.500.
16. White, M. F., Maron, R. & Kahn, C. R. Insulin rapidly stimulates tyrosine phosphorylation of a Mr-185,000 protein in intact cells. Nature 1985; 318: 183-186.
17. Kahn, C. R., White, M. F., Rothenberg, P. L. Isolated DNA encoding an insulin receptor substrate. U.S. Pat. No. 5,260,200. Filed Oct. 15, 1992. Issued Nov. 9, 1993.
18. Sun, X. J. et al. Structure of the insulin receptor substrate IRS-1 defines a unique signal transduction protein. Nature 1991; 352: 73-77.
19. White, M. F., Sun, X. J., Pierce, J. H. DNA encoding an insulin receptor substrate. U.S. Pat. No. 5,858,701. Filed Oct. 3, 1994. Issued Jan. 12, 1999.
20. Sun, X. J. et al. Role of IRS-2 in insulin and cytokine signalling. Nature 1995; 377: 173-177.
21. Burks D J, Wang J, Towery H, Ishibashi O, Lowe D, Riedel H, et al. IRS pleckstrin homology domains bind to acidic motifs in proteins. J Biol Chem 1998 Nov. 20; 273 (47):31061-7.

22. Wu J, Tseng Y D, Xu C F, Neubert T A, White M F, Hubbard S R. Structural and biochemical characterization of the KRLB region in insulin receptor substrate-2. Nat Struct Mol Biol 2008 March 15(3) 251-8.
23. Backer J M, Myers M G, Jr., Shoelson S E, Chin D J, Sun X J, Miralpeix M, et al. Phosphatidylinositol 3'-kinase is activated by association with IRS-1 during insulin stimulation. EMBO J 1992; 11:3469-79.
24. Manning B D, Cantley L C. AKT/PKB signaling: navigating downstream. Cell 2007 Jun. 29; 129 (7):1261-74.
25. Dong X C, Copps K D, Guo S, Li Y, Kollipara R, DePinho R A, et al. Inactivation of hepatic Foxo1 by insulin signaling is required for adaptive nutrient homeostasis and endocrine growth regulation. Cell Metab 2008 July; 8 (1):65-76.
26. Jhala U S, Canettieri G, Screaton R A, Kulkarni R N, Krajewski S, Reed J, et al. cAMP promotes pancreatic beta-cell survival via CREB-mediated induction of IRS2. Genes Dev 2003 Jul. 1; 17 (13):1575-80.
27. Shimano H. SREBP-1c and TFE3, energy transcription factors that regulate hepatic insulin signaling. J Mol Med 2007 May; 85 (5):437-44.
28. Ide T, Shimano H, Yahagi N, Matsuzaka T, Nakakuki M, Yamamoto T, et al. SREBPs suppress IRS-2-mediated insulin signalling in the liver. Nat Cell Biol 2004 April; 6 (4):351-7.
29. Zick Y. Ser/Thr phosphorylation of IRS proteins: a molecular basis for insulin resistance. Sci STKE 2005 Jan. 25; 2005 (268):e4.
30. White M F. Regulating insulin signaling and beta-cell function through IRS proteins. Can J Physiol Pharmacol 2006 July; 84 (7):725-37.
31. Wellen K E, Hotamisligil G S. Inflammation, stress, and diabetes. J Clin Invest 2005 May; 115 (5):1111-9.
32. Withers D J, Gutierrez J S, Towery H, Burks D J, Ren J M, Previs S, et al. Disruption of IRS-2 causes type 2 diabetes in mice. Nature 1998; 391 (6670):900-4.
33. Jonsson J, Carlsson L, Edlund T, Edlund H. Insulin-promoter-factor 1 is required for pancreas development in mice. Nature 1994; 371 (6498):606-9.
34. Weir G C, Bonner-Weir S. A dominant role for glucose in beta cell compensation of insulin resistance. J Clin Invest 2007 January; 117(1):81-3.
35. Krebs, D. L., Hilton, D. J. A new role for SOCS in insulin action. Suppressor of cytokine signaling. Sci STKE. 2003 Feb. 11; (169): PE6.
36. Haj, F. G., Verveer, P. J., Squire, A., Neel, B. G., Bastiaens, P. I. Imaging sites of receptor dephosphorylation by PTP1B on the surface of the endoplasmic reticulum. Science. 2002 Mar. 1; 295(5560):1708-1711
37. Berge, S. M., Bighley, L. D., Monkhouse, D. C. Pharmaceutical salts. J Pharm Sci. 1977 January; 66(1):1-19.
38. Housey, G M, White, M F, Method of Screening Activators and/or Inhibitors of Insulin Receptor Substrate 2. U.S. Pat. No. 8,557,512 B2. Ser. No. 10/541,263. Filed Dec. 31, 2003. Issued Oct. 15, 2013.
39. Housey, G. M., Balash M. (2010) IRS Modulators. US Provisional Patent Application. Filed Jun. 3, 2010.
40. Liu S, Serdula M, Janket S J, Cook N R, Sesso H D, Willett W C, Manson J E, Buring J E. A prospective study of fruit and vegetable intake and the risk of type 2 diabetes in women. Diabetes Care. 2004 December; 27 (12):2993-6.
41. Bazzano L A, Li T Y, Joshipura K J, Hu F B. Intake of fruit, vegetables, and fruit juices and risk of diabetes in women. Diabetes Care. 2008 July; 31 (7):1311-7
42. Montonen J, Jarvinen R, Heliovaara M, Reunanen A, Aromaa A, Knekt P. Food consumption and the incidence of type II diabetes mellitus. Eur J Clin Nutr. 2005 March; 59 (3):441-8.
43. Meyer K A, Kushi L H, Jacobs D R Jr, Slavin J, Sellers T A, Folsom A R. Carbohydrates, dietary fiber, and incident type 2 diabetes in older women. Am J Clin Nutr. 2000 April; 71 (4):921-30.
44. Villegas R, Shu X O, Gao Y T, Yang G, Elasy T, Li H, Zheng W. Vegetable but not fruit consumption reduces the risk of type 2 diabetes in Chinese women. J Nutr. 2008 March; 138 (3):574-80.
45. Carter P, Gray L J, Troughton J, Khunti K, Davies M J. Fruit and vegetable intake and incidence of type 2 diabetes mellitus: systematic review and meta-analysis. BMJ. 2010 Aug. 18; 341:c4229.
46. Muthusamy V S, Saravanababu C, Ramanathan M, Bharathi Raja R, Sudhagar S, Anand S, Lakshmi B S. Inhibition of protein tyrosine phosphatase 1B and regulation of insulin signalling markers by caffeoyl derivatives of chicory (Cichorium intybus) salad leaves. Br J Nutr. 2010 September; 104 (6):813-23.
47. Ahmed N, Tarannum S. Acetylcholinesterase activity in the brain of alloxan diabetic albino rats: Presence of an inhibitor of this enzyme activity in the cerebral extract. Int J Diabetes Dev Ctries. 2009 October; 29 (4):174-7.
48. Muthusamy V S, Anand S, Sangeetha K N, Sujatha S, Arun B, Lakshmi B S. Tannins present in Cichorium intybus enhance glucose uptake and inhibit adipogenesis in 3T3-L1 adipocytes through PTP1B inhibition. Chem Biol Interact. 2008 Jul. 10; 174 (1):69-78.
49. Pushparaj P N, Low H K, Manikandan J, Tan B K, Tan C H. Anti-diabetic effects of Cichorium intybus in streptozotocin-induced diabetic rats. J Ethnopharmacol. 2007 May 4; 111 (2):430-4.
50. Petlevski R, Hadzij a M, Slijepcević M, Juretić D, Petrik J. Glutathione S-transferases and malondialdehyde in the liver of NOD mice on short-term treatment with plant mixture extract P-9801091. Phytother Res. 2003 April; 17 (4):311-4.
51. Petlevski R, Hadzij a M, Slijepcevic M, Juretic D. Effect of 'antidiabetis' herbal preparation on serum glucose and fructosamine in NOD mice. J Ethnopharmacol. 2001 May; 75 (2-3):181-4.
52. Estruch R, Ros E, Salas-Salvado J, Covas M I, D Pharm, Corella D, Arós F, Gómez-Gracia E, Ruiz-Gutiérrez V, Fiol M, Lapetra J, Lamuela-Raventos R M, Serra-Majem L, Pintó X, Basora J, Muñoz M A, Sorlí J V, Martínez J A, Martínez-Gonzalez M A; the PREDIMED Study Investigators. Primary Prevention of Cardiovascular Disease with a Mediterranean Diet. N Engl J Med. 2013 Feb. 25.
53. Mascherpa, D. Carazzone C, Marrubini G, Gazzani G, Papetti A. Identification of phenolic constituents in Cichorium endivia var. crispum and var. latifolium salads by high-performance liquid chromatography with diode array detection and electrospray ionization tandem mass spectrometry. J Agric Food Chem. 2012 Nov. 19; 60 (49):12142-50.
54. Papetti A, Daglia M, Gazzani G. Anti- and pro-oxidant water soluble activity of Cichorium genus vegetables and effect of thermal treatment. J Agric Food Chem. 2002 Jul. 31; 50 (16):4696-704.
55. Diabetes Prevention Program Research Group. Reduction in the Incidence of Type 2 Diabetes with Lifestyle Intervention or Metformin. N Engl J Med 2002 Feb. 7; 346 (6): 393-403

56. Campbell, I W. Metformin—life begins at 50: A symposium held on the occasion of the 43rd Annual Meeting of the European Association for the Study of Diabetes, Amsterdam, The Netherlands, September 2007, The British Journal of Diabetes & Vascular Disease. 2007 Sep. 7: 247-252.
57. Papetti A, Daglia M, Aceti C, Sordelli B, Spini V, Carazzone C, Gazzani G. Hydroxycinnamic acid derivatives occurring in *Cichorium endivia* vegetables. J Pharm Biomed Anal. 2008 Sep. 29; 48 (2):472-6.
58. Pushparaj P, Tan C H, Tan B K. Effects of Averrhoa bilimbi leaf extract on blood glucose and lipids in streptozotocin-diabetic rats. J Ethnopharmacol. 2000 September; 72 (1-2):69-76.
59. Süntar I, Kiipeli Akkol E, Keles H, Yesilada E, Sarker S D, Baykal T. Comparative evaluation of traditional prescriptions from *Cichorium intybus* L. for wound healing: stepwise isolation of an active component by in vivo bioassay and its mode of activity. J Ethnopharmacol. 2012 Aug. 30; 143 (1):299-309.
60. Pinent M, Blay M, Bladé M C, Salvado M J, Arola L, Ardévol A. Grape seed-derived procyanidins have an antihyperglycemic effect in streptozotocin-induced diabetic rats and insulinomimetic activity in insulin-sensitive cell lines. Endocrinology. 2004 November; 145 (11): 4985-90.
61. Xavier-Filho J, Oliveira A. E. A., Silva L. B. da, Azevedo C. R., Venancio T. M., Machado O. L. T., Oliva M. L., Fernandes K. V. S., Xavier-Neto J. Plant insulin or glucokinin: a conflicting issue. Braz. J. Plant Physiol. 2003 May/August; 15 (2):67-78.
62. Andrade-Cetto A, Heinrich M. Mexican plants with hypoglycaemic effect used in the treatment of diabetes. J Ethnopharmacol. 2005 Jul. 14; 99 (3):325-48.
63. Diaz-Flores M, Angeles-Mejia S, Baiza-Gutman L A, Medina-Navarro R, Hernandez-Saavedra D, Ortega-Camarillo C, Roman-Ramos R, Cruz M, Alarcon-Aguilar F J. Effect of an aqueous extract of Cucurbita ficifolia Bouché on the glutathione redox cycle in mice with STZ-induced diabetes. J Ethnopharmacol. 2012 Oct. 31; 144 (1):101-8.
64. Deutschländer M S, Lall N, Van de Venter M, Hussein A A. Hypoglycemic evaluation of a new triterpene and other compounds isolated from Euclea undulata Thunb. var. myrtina (Ebenaceae) root bark. J Ethnopharmacol. 2011 Feb. 16; 133 (3):1091-5.
65. Acosta-Patiño J L, Jiménez-Balderas E, Juárez-Oropeza M A, Diaz-Zagoya J C. Hypoglycemic action of Cucurbita ficifolia on Type 2 diabetic patients with moderately high blood glucose levels. J Ethnopharmacol. 2001 September; 77(1):99-101.
66. Van de Venter M, Roux S, Bungu L C, Louw J, Crouch N R, Grace O M, Maharaj V, Pillay P, Sewnarian P, Bhagwandin N, Folb P. Antidiabetic screening and scoring of 11 plants traditionally used in South Africa. J Ethnopharmacol. 2008 Sep. 2; 119 (1):81-6.
67. Vinson J A, Burnham B R, Nagendran M V. Randomized, double-blind, placebo-controlled, linear dose, crossover study to evaluate the efficacy and safety of a green coffee bean extract in overweight subjects. Diabetes Metab Syndr Obes. 2012; 5:21-7.
68. Hamza N, Berke B, Cheze C, Le Garrec R, Lassalle R, Agli A N, Robinson P, Gin H, Moore N. Treatment of high fat diet induced type 2 diabetes in C57BL/6J mice by two medicinal plants used in traditional treatment of diabetes in the east of Algeria. J Ethnopharmacol. 2011 Jan. 27; 133 (2):931-3.
69. Ahmed A B, Rao A S, Rao M V. In vitro callus and in vivo leaf extract of Gymnema sylvestre stimulate β-cells regeneration and anti-diabetic activity in Wistar rats. Phytomedicine. 2010 November; 17 (13):1033-9.
70. Roman-Ramos R, Flores-Saenz J L, Alarcon-Aguilar F J. Anti-hyperglycemic effect of some edible plants. J Ethnopharmacol. 1995 Aug. 11; 48 (1):25-32.
71. Zhang B, Salituro G, Szalkowski D, Li Z, Zhang Y, Royo I, Vilella D, Diez M T, Pelaez F, Ruby C, Kendall R L, Mao X, Griffin P, Calaycay J, Zierath J R, Heck J V, Smith R G, Moller D E. Discovery of a small molecule insulin mimetic with antidiabetic activity in mice. Science. 1999 May 7; 284(5416):974-7.
72. Ghamarian A, Abdollahi M, Su X, Amiri A, Ahadi A, Nowrouzi A. Effect of chicory seed extract on glucose tolerance test (GTT) and metabolic profile in early and late stage diabetic rats. Dam. 2012 Oct. 15; 20(1):56.
73. DuPont M S, Mondin Z, Williamson G, Price K R. Effect of variety, processing, and storage on the flavonoid glycoside content and composition of lettuce and endive. J Agric Food Chem. 2000 September; 48 (9):3957-64.
74. Tousch D, Lajoix A D, Hosy E, Azay-Milhau J, Ferrare K, Jahannault C, Cros G, Petit P. Chicoric acid, a new compound able to enhance insulin release and glucose uptake. Biochem Biophys Res Commun. 2008 Dec. 5; 377 (1):131-5.
75. Kamel Z H, Daw I, Marzouk M. Effect of *Cichorium endivia* leaves on some biochemical parameters in streptozotocin-induced diabetic rats. Aus J Basic and App Sci. 2011; 5 (7):387-96
76. Park K J, de Oliveira R A, Brod F P R. Drying Operational Parameters Influence on Chicory Roots Drying and Inulin Extraction. Food and Bioproducts Processing. 2007 September; 85 (3); 184-92
77. Hagel J M, Yeung E C, Facchini P J. Got milk? The secret life of laticifers. Trends Plant Sci. 2008 December; 13(12):631-9.
78. Lewinsohn T M. The geographical distribution of plant latex. Chemoecology 1991; 2(1):64-8
79. Montagut G, Onnockx S, Vaqué M, Bladé C, Blay M, Fernández-Larrea J, Pujadas G, Salvadó M J, Arola L, Pirson I, Ardévol A, Pinent M. Oligomers of grape-seed procyanidin extract activate the insulin receptor and key targets of the insulin signaling pathway differently from insulin. J Nutr Biochem. 2010 June; 21 (6):476-81.
80. Obanda D N, Hernandez A, Ribnicky D, Yu Y, Zhang X H, Wang Z Q, Cefalu W T. Bioactives of *Artemisia dracunculus* L. mitigate the role of ceramides in attenuating insulin signaling in rat skeletal muscle cells. Diabetes. 2012 March; 61 (3):597-605.
81. Pushparaj P N, Tan B K, Tan C H. The mechanism of hypoglycemic action of the semi-purified fractions of Averrhoa bilimbi in streptozotocin-diabetic rats. Life Sci. 2001 Dec. 21; 70 (5):535-47.
82. Layne J. Characterization and comparison of the chromatographic performance of conventional, polar-embedded, and polar-endcapped reversed-phase liquid chromatography stationary phases. Journal of Chromatography A, 2002 957: 149-164.
83. Wolfender J L, Ndjoko K, Hostettmann, K. Liquid chromatography with ultraviolet absorbance—mass spectrometric detection and with nuclear magnetic resonance spectrometry: a powerful combination for the on-line structural investigation of plant metabolites. Journal of Chromatography A 1000 2003: 437-455.

84. Buszewski B, Noga S. Hydrophilic interaction liquid chromatography (HILIC)—a powerful separation technique. Analytical and bioanalytical chemistry, 2012; 402 (1): 231-247.
85. Fahey J W, Zalcmann A T, Talalay P. The chemical diversity and distribution of glucosinolates and isothiocyanates among plants. Phytochemistry. 2001 January; 56 (1):5-51.
86. Oxford Dictionary of Chemistry (7 ed.) 2016, Oxford University Press

We claim:

1. A method of treating an IRS mediated disease or condition comprising administering an effective amount of a pharmaceutical composition or nutritional supplement to a subject in need thereof,
wherein the pharmaceutical composition or nutritional supplement comprises:
an aqueous extract of *Artemisia dracunculus;*
an aqueous extract of *Cichoria endivia*; and
an aqueous extract of *Lactuca sativa*; and
wherein the pharmaceutical composition or nutritional supplement is in tablet, capsule, or powder form.

2. The method of claim 1 wherein the IRS mediated disease or condition is diabetes, pre-diabetes, metabolic syndrome, insulin resistance, or dementia.

3. The method of claim 1 which further comprises administering an antidiabetic agent, insulin, metformin, exenatide, a sulfonylurea, vildagliptin, sitagliptin, a DPP4 inhibitor, meglitinide, exendin-4, liraglutide, a thiazolidinedione, empagliflozin, canagliflozin, dapagliflozin, or a GLP1 agonist.

4. The method of claim 1 wherein the pharmaceutical composition or nutritional supplement is administered orally twice per day, 30-60 minutes before meals.

5. A method of stimulating IRS2-dependent signal transduction in a subject in need thereof comprising administering to the subject an effective amount of a pharmaceutical composition or nutritional supplement,
wherein the pharmaceutical composition or nutritional supplement comprises:
an aqueous extract of *Artemisia dracunculus;*
an aqueous extract of *Cichoria endivia*; and
an aqueous extract of *Lactuca sativa;*
wherein the extracts of *Artemisia dracunculus, Cichoria endivia*, and *Lactuca sativa* are in a ratio of about 1:1,375:24 (w/w/w), respectively, and
wherein the pharmaceutical composition or nutritional supplement is in tablet, capsule, or powder form.

6. A method of stimulating IRS2-dependent signal transduction comprising contacting a cell with a botanical extract,
wherein the botanical extract provides greater than $3.6 \times 10^4$ Insulin Equivalent units in 1 milliliter comprising aqueous extracts from *Artemisia dracunculus, Cichoria endivia*, and *Lactuca sativa*.

7. A method of stimulating IRS2-dependent signal transduction comprising contacting a cell with a pharmaceutical composition or nutritional supplement,
wherein the pharmaceutical composition or nutritional supplement comprises:
an aqueous extract of *Artemisia dracunculus;*
an aqueous extract of *Cichoria endivia*; and
an aqueous extract of *Lactuca sativa*; and
wherein the pharmaceutical composition or nutritional supplement is in tablet, capsule, or powder form.

* * * * *

UNITED STATES PATENT AND TRADEMARK OFFICE
CERTIFICATE OF CORRECTION

PATENT NO. : 11,633,446 B2
APPLICATION NO. : 16/612545
DATED : April 25, 2023
INVENTOR(S) : Gerard M. Housey and Monica Elizabeth Balash It is certified that error appears in the above-identified patent and that said Letters Patent is hereby corrected as shown below:

In the Claims

In Claim 6, Line 19, the '·' after 3.6 should read --×--.

Signed and Sealed this
First Day of August, 2023

Katherine Kelly Vidal
Director of the United States Patent and Trademark Office